(12) United States Patent
Ohno et al.

(10) Patent No.: US 8,778,205 B2
(45) Date of Patent: Jul. 15, 2014

(54) PROCESSING METHOD AND PROCESSING SYSTEM

(75) Inventors: Tsuyoshi Ohno, Tokyo (JP); Toshihiko Kikuchi, Nirasaki (JP); Machi Moriya, Nirasaki (JP); Yoshitaka Saita, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 495 days.

(21) Appl. No.: 12/588,395

(22) Filed: Oct. 14, 2009

(65) Prior Publication Data

US 2010/0133231 A1 Jun. 3, 2010

Related U.S. Application Data

(62) Division of application No. 10/869,913, filed on Jun. 18, 2004, now abandoned.

(30) Foreign Application Priority Data

Jun. 20, 2003 (JP) .................................. 2003-177237
Jun. 7, 2004 (JP) .................................. 2004-168649

(51) Int. Cl.
| | | |
|---|---|---|
| B44C 1/22 | (2006.01) | |
| C03C 15/00 | (2006.01) | |
| C03C 25/68 | (2006.01) | |
| C23F 1/00 | (2006.01) | |
| H01L 21/302 | (2006.01) | |
| H01L 21/461 | (2006.01) | |

(52) U.S. Cl.
USPC .................. 216/67; 216/58; 438/689; 438/714

(58) Field of Classification Search
None
See application file for complete search history.

(56) References Cited

U.S. PATENT DOCUMENTS

| | | |
|---|---|---|
| 5,304,437 A | 4/1994 | Tennant |
| 5,399,229 A | 3/1995 | Stefani et al. |
| 6,081,334 A | 6/2000 | Grimbergen et al. |
| 6,358,676 B1 | 3/2002 | Wu |
| 6,813,032 B1 | 11/2004 | Hunter |
| 6,830,649 B2 | 12/2004 | Kagoshima et al. |
| 6,858,361 B2 * | 2/2005 | Mui et al. ........................ 430/30 |
| 2003/0106642 A1 * | 6/2003 | Fairbairn et al. .......... 156/345.24 |

(Continued)

FOREIGN PATENT DOCUMENTS

| | | |
|---|---|---|
| JP | 05-160074 | 6/1993 |
| JP | 10-172942 | 6/1998 |

(Continued)

OTHER PUBLICATIONS

Patent Office Notification to submit Argument mailed on Jan. 26, 2006, in corresponding Korean Patent Application No. 0045839.

(Continued)

*Primary Examiner* — Nadine Norton
*Assistant Examiner* — Stephanie Duclair
(74) *Attorney, Agent, or Firm* — Finnegan, Henderson, Farabow, Garrett & Dunner, L.L.P.

(57) ABSTRACT

The present invention is a processing method including a processing step of performing predetermined processing for a workpiece; an unnecessary portion removal step of removing an unnecessary portion produced on a surface of the workpiece due to the predetermined processing; and a surface structure evaluation step of evaluating a surface structure of the workpiece from which the unnecessary portion has been removed by the unnecessary portion removal step.

2 Claims, 26 Drawing Sheets

(56) References Cited

U.S. PATENT DOCUMENTS

| | | |
|---|---|---|
| 2003/0114011 A1 | 6/2003 | Kagoshima |
| 2005/0252884 A1 | 11/2005 | Lam et al. |
| 2006/0124243 A1 | 6/2006 | Kagoshima et al. |
| 2008/0165367 A1 | 7/2008 | Moriya et al. |

FOREIGN PATENT DOCUMENTS

| | | |
|---|---|---|
| JP | 10-233374 | 9/1998 |
| JP | 2000-352827 | 12/2000 |
| JP | 2002-260944 | 9/2002 |
| JP | 2003-17471 | 1/2003 |
| JP | 2005510083 | 1/2005 |
| WO | WO 03/044851 A2 | 5/2003 |

OTHER PUBLICATIONS

First Notification of Reasons for Rejection issued on Aug. 18, 2006, in corresponding Chinese Patent Application No. 2004100598967.

Notification of Reasons for Rejection issued on Jul. 27, 2010, in corresponding Japanese Patent Application No. 2004-168649 (3 pages).

English translation of Notification of Reasons for Rejection issued on Jul. 27, 2010, in corresponding Japanese Patent Application No. 2004-168649 (3 pages).

Office Action regarding Taiwanese Application No. 09311748, dated Oct. 19, 2010 (6 pgs).

English translation of Office Action regarding Taiwanese Application No. 09311748, dated Oct. 19, 2010 (3 pgs).

\* cited by examiner

FIG.6
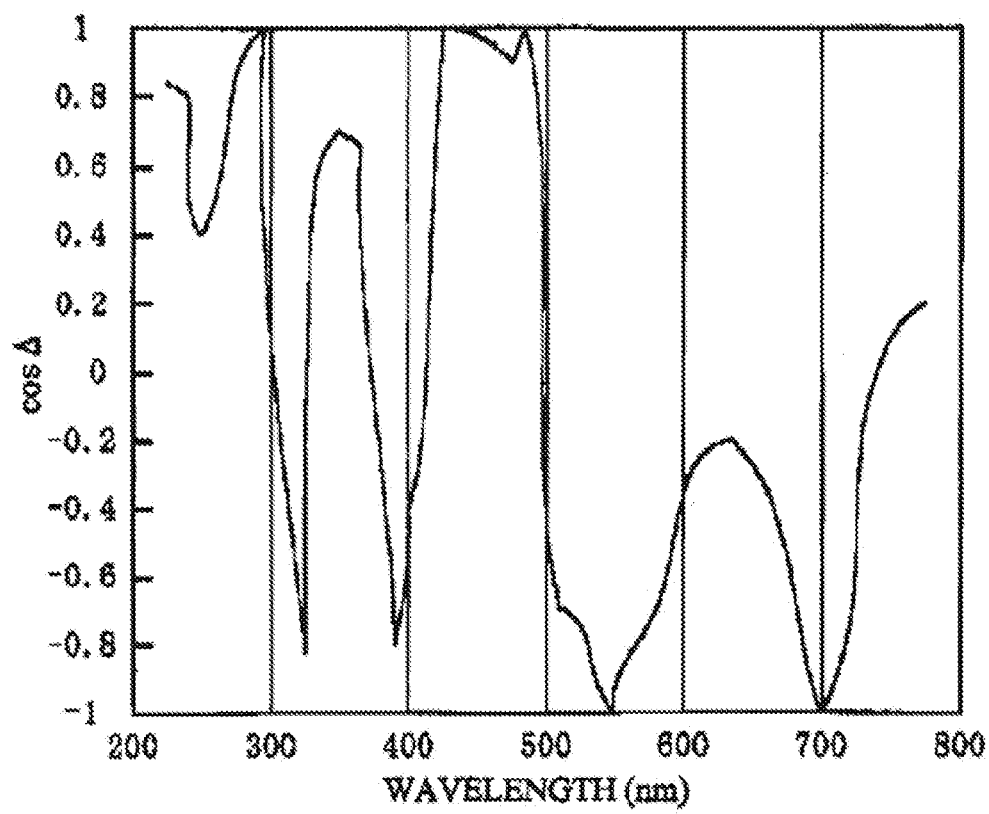
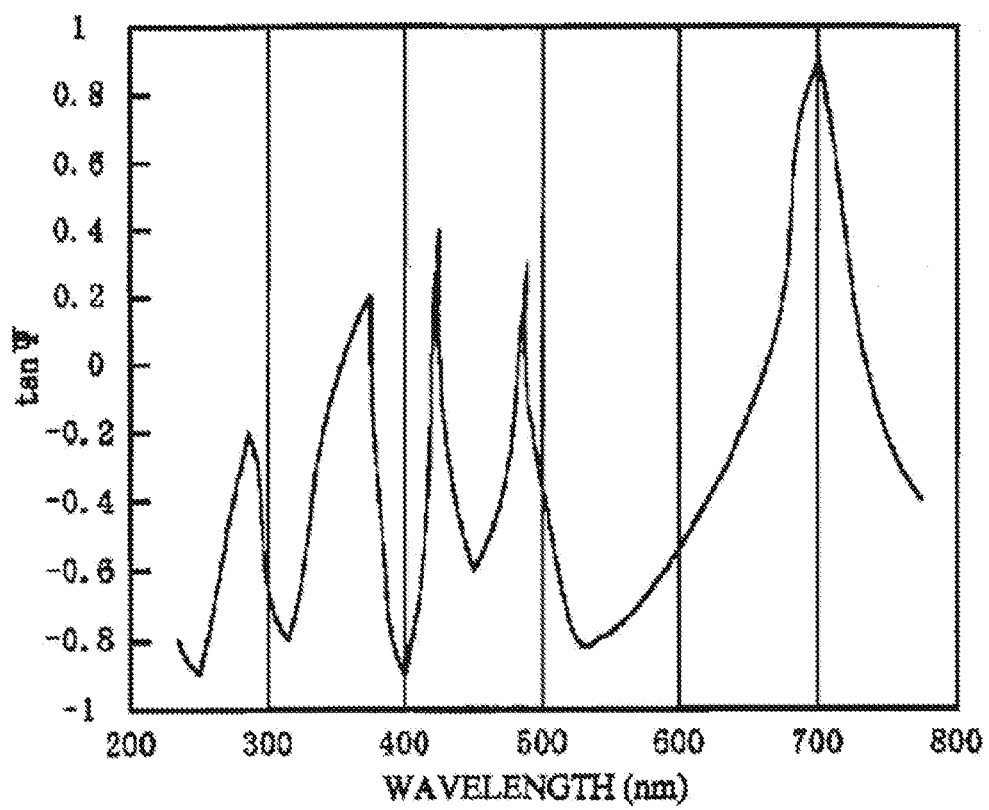

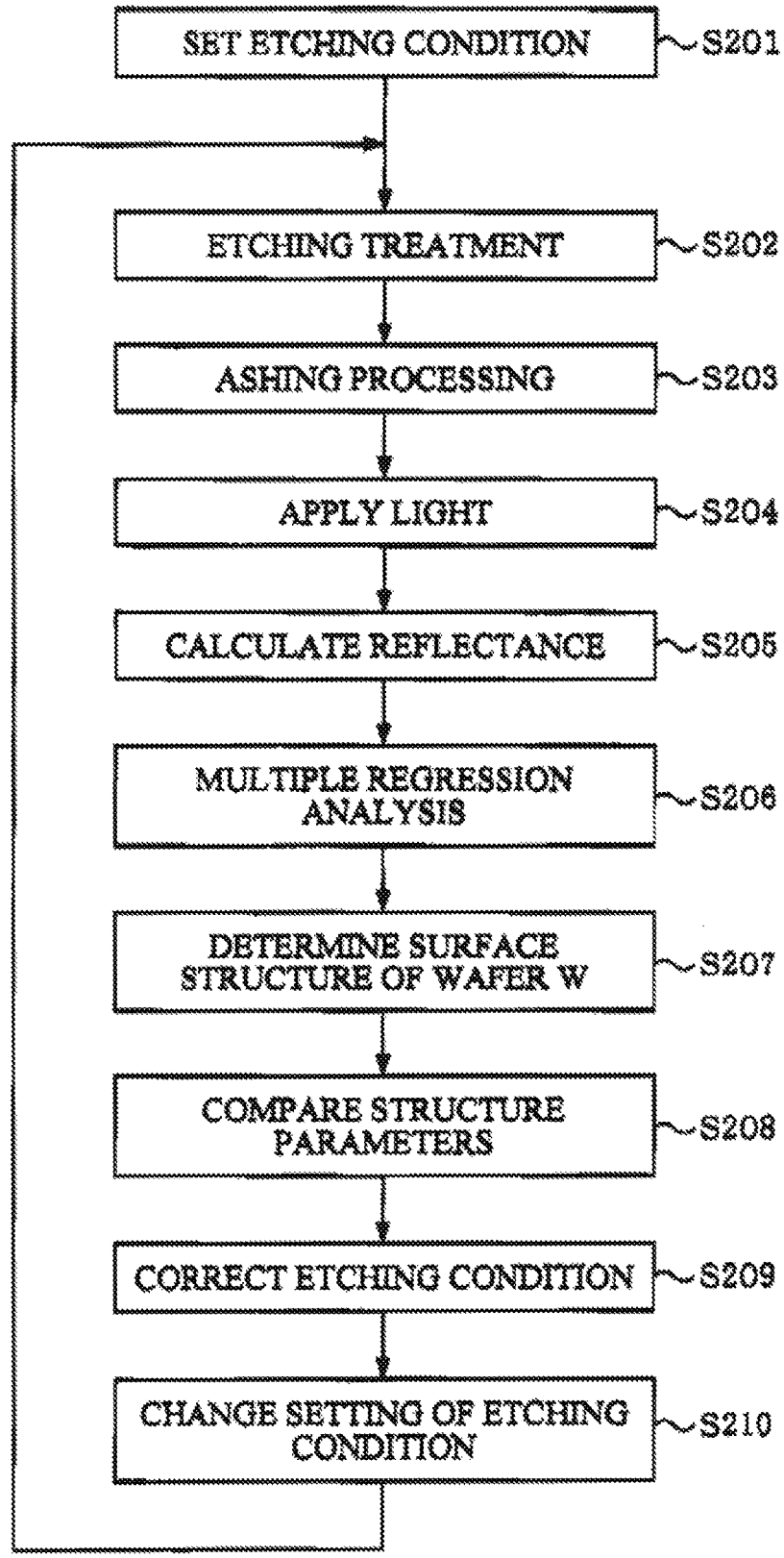

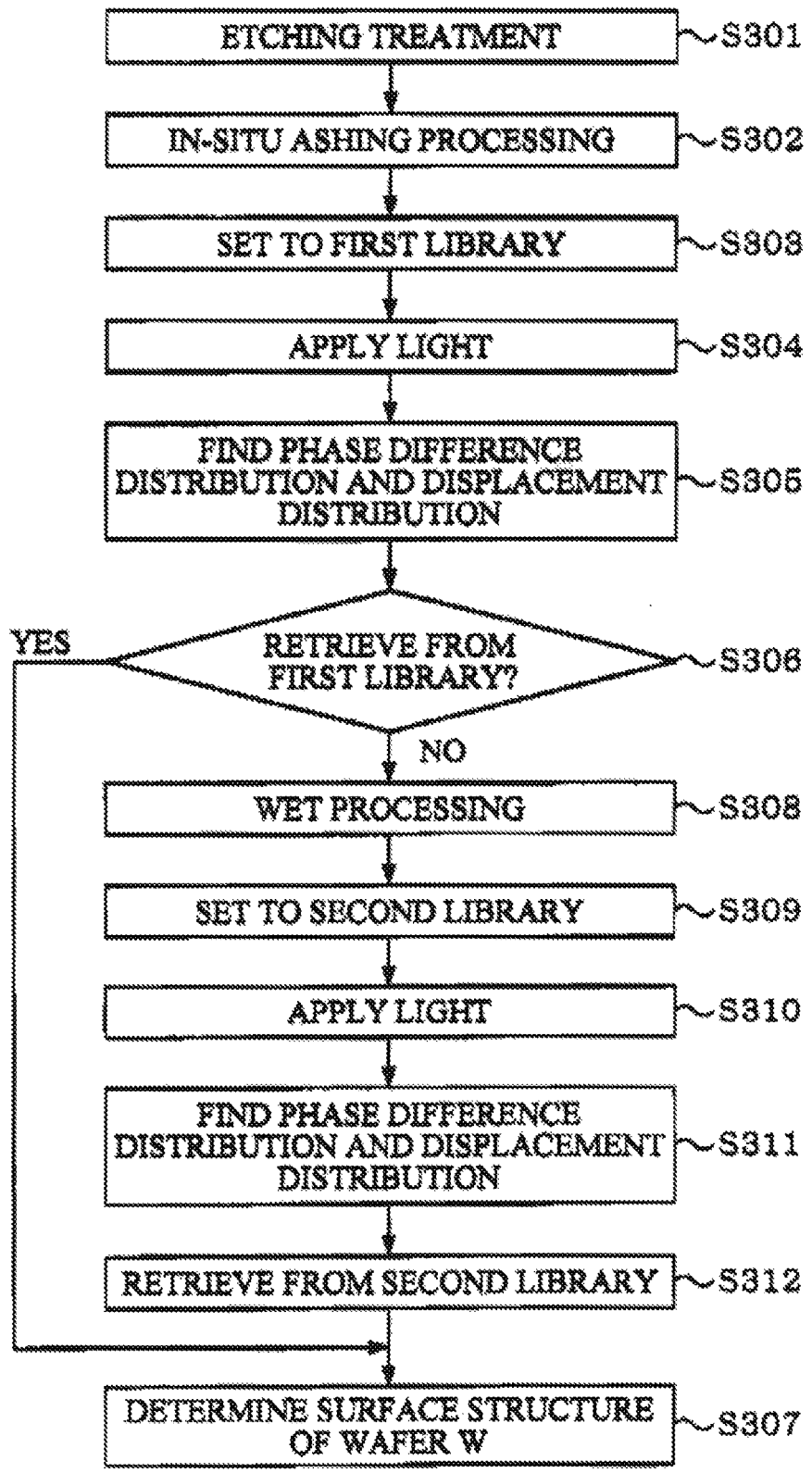

FIG.24(A)

| DEPTH ELIMINATION AMOUNT (nm) | ETCHING TIME (s) |
|---|---|
| 180.0 | 36 |
| 185.0 | 37 |
| 190.0 | 38 |
| 195.0 | 39 |
| 200.0 | 40 |
| 205.0 | 41 |
| 210.0 | 42 |
| 215.0 | 43 |

FIG.24(B)

| | | ETCHING TIME (s) | | | | | | | |
|---|---|---|---|---|---|---|---|---|---|
| | | 35 | 36 | 37 | 38 | 39 | 40 | 41 | 42 | 43 |
| FLOW RATE OF GAS (cm3/min) | 34 | 31.0 | 32.0 | 33.0 | 34.0 | 35.0 | 36.0 | 37.0 | 38.0 | 39.0 |
| | 36 | 33.0 | 34.0 | 35.0 | 36.0 | 37.0 | 38.0 | 39.0 | 40.0 | 41.0 |
| | 38 | 35.0 | 36.0 | 37.0 | 38.0 | 39.0 | 40.0 | 41.0 | 42.0 | 43.0 |
| | 40 | 37.0 | 38.0 | 39.0 | 40.0 | 41.0 | 42.0 | 43.0 | 44.0 | 45.0 |
| | 42 | 39.0 | 40.0 | 41.0 | 42.0 | 43.0 | 44.0 | 45.0 | 46.0 | 47.0 |
| | 44 | 41.0 | 42.0 | 43.0 | 44.0 | 45.0 | 46.0 | 47.0 | 48.0 | 49.0 |
| | 46 | 43.0 | 44.0 | 45.0 | 46.0 | 47.0 | 48.0 | 49.0 | 50.0 | 51.0 |
| | 48 | 45.0 | 46.0 | 47.0 | 48.0 | 49.0 | 50.0 | 51.0 | 52.0 | 53.0 |
| | 50 | 47.0 | 48.0 | 49.0 | 50.0 | 51.0 | 52.0 | 53.0 | 54.0 | 55.0 |

LINE WIDTH ELIMINATION AMOUNT (nm)

PROCESSING METHOD AND PROCESSING SYSTEM

This is a divisional of application Ser. No. 10/869,913, filed Jun. 18, 2004, now abandoned which is Incorporated herein by reference.

BACKGROUND OF THE INVENTION

1. Field of the Invention

The present invention relates to a processing method and a processing system. In particular, the present invention relates to a processing method and a processing system each for accurately nondestructively evaluating by Scatterometry a surface structure of a workpiece after predetermined processing and for controlling processing conditions based on the evaluated surface structure.

2. Description of the Related Art

In these days, the semiconductor integrated circuits are increasing reduced in size, giving rise to a need for forming the circuit pattern on a wafer surface more finely. To form such a finer circuit pattern, it is necessary to accurately evaluate the structure of the wafer surface, for example, the structure of the wafer surface after an etching processing or the like at the manufacturing process step.

Conventionally, to evaluate the structure of the wafer surface after the etching processing, such a method has mainly been taken that the cross section of a cleaved wafer is observed under a scanning electron microscope (SEM) and photographed. This method, however, has a disadvantage that the wafer itself needs to be broken to form a wafer cross section that is observation object.

Hence, in order to nondestructively evaluate the structure of the wafer surface after the etching processing, the present inventor considered whether Scatterometry such as Reflectometry, Ellipsometry, or the like which have conventionally been used for evaluation or the like of a resist pattern formed on the wafer surface is applicable to evaluation of the structure of the wafer surface after the etching processing (see, for example, Japanese Patent Application Laid-open No. 2002-260994).

However, since the wafer surface after the etching processing has unnecessary portions with various shapes and compositions, such as a polymer attached to the surface, a damaged layer formed within the surface region of a wafer W, and a deteriorated layer and a hard layer formed within the surface region of a resist, and so on, its optical constant n value (refractive index) and k value (absorption coefficient) cannot be specified.

It is difficult to evaluate by Scatterometry such a surface structure of the wafer W whose optical constant cannot be specified.

Besides, a concrete method for evaluating the surface structure of a wafer and a concrete control method of processing conditions based on the evaluation are still undeveloped.

SUMMARY OF THE INVENTION

The present invention has been developed in view of the above situation, and it is an object thereof to provide a processing method and a processing system each capable of accurately nondestructively evaluating by Scatterometry a surface structure of a workpiece after predetermined processing.

It is another object of the present invention to provide a concrete processing method and processing system each for evaluating a surface structure of a workpiece by Scatterometry, and to a processing method and a processing system each for controlling processing conditions based on the surface structure of the workpiece evaluated by Scatterometry.

To attain the above objects, a processing method of the present invention comprises: a processing step of performing predetermined processing for a workpiece; an unnecessary portion removal step of removing an unnecessary portion produced on a surface of the workpiece due to the predetermined processing; and a surface structure evaluation step (a structure evaluation step) of evaluating a surface structure of the workpiece from which the unnecessary portion has been removed by the unnecessary portion removal step.

The processing method may further comprises a control step of controlling at least one of parameters of a processing condition of the predetermined processing based the surface structure of the workpiece evaluated by the surface structure evaluation step.

The predetermined processing may be an etching processing of etching the workpiece using a resist as a mask to form a predetermined pattern in the surface of the workpiece.

The unnecessary portion removal step may be a step of removing a deteriorated layer and/or a hard layer formed in the resist in the etching processing.

The unnecessary portion removal step may be a step of removing a damaged layer formed within a surface region of the predetermined pattern in the etching processing.

The unnecessary portion removal step may be a step of removing a polymer attached to the surface of the workpiece in the etching processing.

The unnecessary portion removal step may be a step of removing a resist having a cross-sectional shape changed by the etching processing. It should be noted that the unnecessary portion removal step may be a step of removing a reaction product deposited on the surface of the workpiece by the etching processing.

The surface structure evaluation step may be a step of measuring by Scatterometry a predetermined physical quantity of the workpiece from which the unnecessary portion has been removed by the unnecessary portion removal step and estimating the surface structure of the workpiece from the measured predetermined physical quantity.

To attain the above objects, a processing method according to another aspect of the present invention comprises: a processing step of performing predetermined processing for a workpiece; an unnecessary portion removal step of removing an unnecessary portion produced on a surface of the workpiece due to the predetermined processing; and a surface structure evaluation step (a structure evaluation step) of evaluating a first surface structure of the workpiece from which the unnecessary portion has been removed by the unnecessary portion removal step, wherein subsequent to the processing step of performing predetermined processing, the first surface structure evaluation step is performed, and if the evaluation in the first surface structure evaluation step is a failure, the unnecessary portion removal step is performed, and a second surface structure evaluation step is performed for the workpiece from which the unnecessary portion has been removed.

The processing method may further comprises a data switching step of switching from data used in the first surface structure evaluation step to data based on a shape after the unnecessary portion removal in the second surface structure evaluation step.

To attain the above objects, a processing system according to another aspect of the present invention comprises: a processing apparatus for performing predetermined processing for a workpiece; an unnecessary portion removal apparatus for removing an unnecessary portion produced on a surface of the workpiece for which the predetermined processing has been performed; a surface structure evaluation apparatus (a structure evaluation apparatus) for evaluating a surface structure of the workpiece from which the unnecessary portion has been removed by the unnecessary portion removal apparatus; a carrier apparatus for carrying the workpiece into/out of each of the apparatuses; and a control apparatus for controlling the processing apparatus, the unnecessary portion removal apparatus, the surface structure evaluation apparatus, and the carrier apparatus.

To attain the above objects, a processing system according to still another aspect of the present invention comprises: a processing apparatus for performing predetermined processing for a workpiece and removing an unnecessary portion produced on a surface of the workpiece due to the predetermined processing; a surface structure evaluation apparatus (a structure evaluation apparatus) for evaluating a surface structure of the workpiece from which the unnecessary portion has been removed by the processing apparatus; a carrier apparatus for carrying the workplace into/out of each of the apparatuses; and a control apparatus for controlling the processing apparatus, the surface structure evaluation apparatus, and the carrier apparatus.

The processing apparatus for performing the predetermined processing may be a plasma etching apparatus.

The unnecessary portion removal apparatus for removing an unnecessary portion may be a wet processing apparatus. It should be noted that the unnecessary portion removal apparatus for removing an unnecessary portion may be a dry processing apparatus.

The surface structure evaluation apparatus for evaluating a surface structure of the workpiece may perform evaluation by Scatterometry.

The control apparatus may control at least one of parameters of a processing condition of the predetermined processing based the surface structure of the workpiece evaluated by the surface structure evaluation apparatus.

The control apparatus may monitor an evaluation operation in the surface structure evaluation apparatus and conduct a control such that if the control apparatus determines that the evaluation operation is a failure, the control apparatus carries a workpiece under processing at the time of the determination of the failure into the unnecessary portion removal apparatus for removal of the unnecessary portion and carries the workpiece again into the surface structure evaluation apparatus for evaluation of the surface structure.

The control apparatus may determine that the evaluation operation is a failure if the evaluation in the surface structure evaluation apparatus has failed to derive an optimum solution within a predetermined period.

The control apparatus may determine that the evaluation operation is a failure if the evaluation in the surface structure evaluation apparatus has failed to derive an optimum solution from a library.

When the control apparatus makes the determination of the failure, the control apparatus may stop processing or operation in each of the apparatuses for workpieces other than the workpiece.

To attain the above objects, a processing method according to yet another aspect of the present invention comprises: an etching step of performing an etching processing for a workpiece; a surface structure measurement step (a structure measurement step) of measuring using Scatterometry a dimension of a surface structure of the workpiece processed in the etching step; and a step of comparing the dimension of the surface structure measured in the surface structure measurement step to a previously set permissible value and deciding continuation or suspension of the etching processing based on the comparison result. It should be noted that the "surface structure of the workpiece" also includes a three-dimensional surface structure.

The surface structure measurement step may measure dimensions at least in two dimensional directions of the surface structure of the workpiece.

The surface structure measurement step may measure dimensions in a depth direction and a horizontal direction of the surface structure of the workpiece.

The etching step and the surface structure measurement step may be performed using a test workpiece having a structure simpler than that of a workpiece to be a product.

To attain the above objects, a processing system according to another aspect of the present invention comprises: an etching processing apparatus for performing an etching processing for a workpiece; a surface structure measurement apparatus (a structure measurement apparatus) for measuring using Scatterometry a dimension of a surface structure of the workpiece for which the etching processing has been performed; and a control apparatus for comparing the measured dimension of the surface structure to a previously set permissible value and deciding continuation or suspension of the etching processing in the etching processing apparatus based on the comparison result.

The surface structure measurement apparatus may measure dimensions at least in two dimensional directions of the surface structure of the workpiece. Further, the surface structure measurement apparatus may measure dimensions in a depth direction and a horizontal direction of the surface structure of the workpiece.

The surface structure measurement apparatus may measure the dimension of the surface structure of the workpiece using a test workpiece having a structure simpler than that of a workpiece to be a product.

To attain the above objects, a processing method according to yet another aspect of the present invention comprises: a surface structure measurement step (a structure measurement step) of measuring using Scatterometry a dimension of a surface structure of the workpiece before an etching processing; a processing condition setting step of setting a processing condition at the time of an etching processing based on the measurement result of the dimension of the surface structure so that the surface structure of the workpiece after the etching processing has a desired dimension; and thereafter, an etching step of performing an etching processing for the workpiece under the set processing condition.

In the processing method, correlation data between the processing condition at the time of the etching processing and an elimination amount of the surface structure of the workpiece by the etching processing may be obtained in advance, and the processing condition setting step may set the processing condition based on the measurement result of the dimension of the surface structure and the correlation data.

The processing condition setting step may set the processing condition so that dimensions at least in two dimensional directions of the surface structure after the etching processing are desired dimensions.

The processing condition setting step may set a plurality of processing conditions at the time of the etching processing.

The processing condition setting step may set an etching processing time based on the measurement result of the dimension of the surface structure so that a dimension in a depth direction in the surface structure after the etching processing is a desired dimension; and a supply flow rate of an etching gas based on the set etching processing time so that a dimension in a horizontal direction in the surface structure after the etching processing is a desired dimension.

To attain the above objects, a processing system according to still another aspect of the present invention comprises: an etching processing apparatus for performing an etching processing for the workpiece; a surface structure measurement apparatus (a structure measurement apparatus) for measuring using Scatterometry a dimension of a surface structure of the workpiece before the etching processing; and a control apparatus for setting a processing condition at the time of the etching processing based on the measurement result of the dimension of the surface structure so that the surface structure of the workpiece after the etching processing has a desired dimension.

The control apparatus may store correlation data between the processing condition at the time of the etching processing and an elimination amount of the surface structure of the workpiece by the etching processing; and the control apparatus may set the processing condition based on the measurement result of the dimension of the surface structure and the correlation data.

The control apparatus may set the processing condition so that dimensions at least in two dimensional directions of the surface structure after the etching processing are desired dimensions.

The control apparatus may set a plurality of processing conditions at the time of the etching processing.

The control apparatus may set an etching processing time based on the measurement result of the dimension of the surface structure so that a dimension in a depth direction in the surface structure after the etching processing is a desired dimension; and a supply flow rate of an etching gas based on the set etching processing time so that a dimension in a horizontal direction in the surface structure after the etching processing is a desired dimension.

BRIEF DESCRIPTION OF THE DRAWING

FIG. 6 is a diagram showing the cosine of the phase difference, cos Δ at each wavelength and a graph showing the tangent of the amplitude displacement, tan Ψ, at each wavelength, registered in the library stored in the library storage unit according to the first and third embodiments of the present invention;

FIG. 13 is a flowchart showing a processing operation according to the second embodiment of the present invention;

FIG. 15 is a flowchart showing a processing operation according to the third embodiment of the present invention;

FIGS. 24A and 24B are tables showing correlation data between etching conditions and the elimination amount by the etching processing;

DETAILED DESCRIPTION OF THE INVENTION

First Embodiment

A processing apparatus 1 according to a first embodiment of the present invention will be described below with reference to the drawings.

Figure 1:
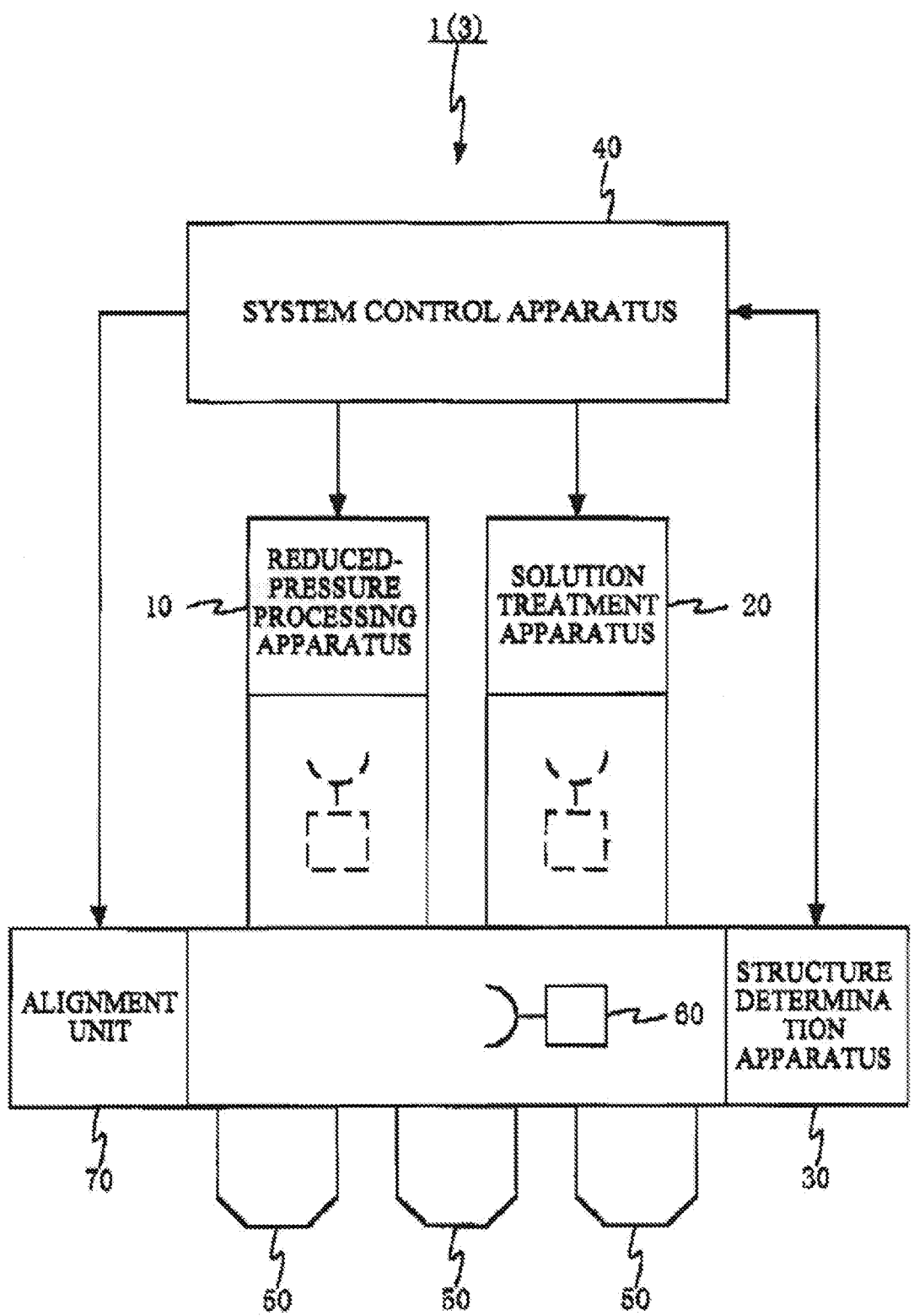
FIG. 1 is a diagram showing the configuration of a processing system according to a first and a third embodiment of the present invention.

The processing system 1, as shown in FIG. 1, is composed of a reduced-pressure processing apparatus 10, a solution treatment apparatus 20 (solution processing apparatus 20), a structure determination apparatus 30, a system control apparatus 40, load ports 50 which mount cassettes housing a plurality of wafers W thereon and form carry in/out portions for the wafers W, a carrier mechanism 60 for carrying the wafers W to the reduced-pressure processing apparatus 10 and so on, and an alignment unit 70 for aligning the wafer W.

The processing system 1 performs an etching processing for the wafer W that is a workpiece and determines (evaluates) by Ellipsometry the surface structure of the wafer W after the etching processing. Note that, as shown in FIG. 10, the wafer W is made of, for example, silicon, a $SiO_2$ layer 5 is formed within the surface region of the wafer W, and further a resist layer 6 in a predetermined pattern is formed on the $SiO_2$ layer 5 on the wafer W.

Figure 2:
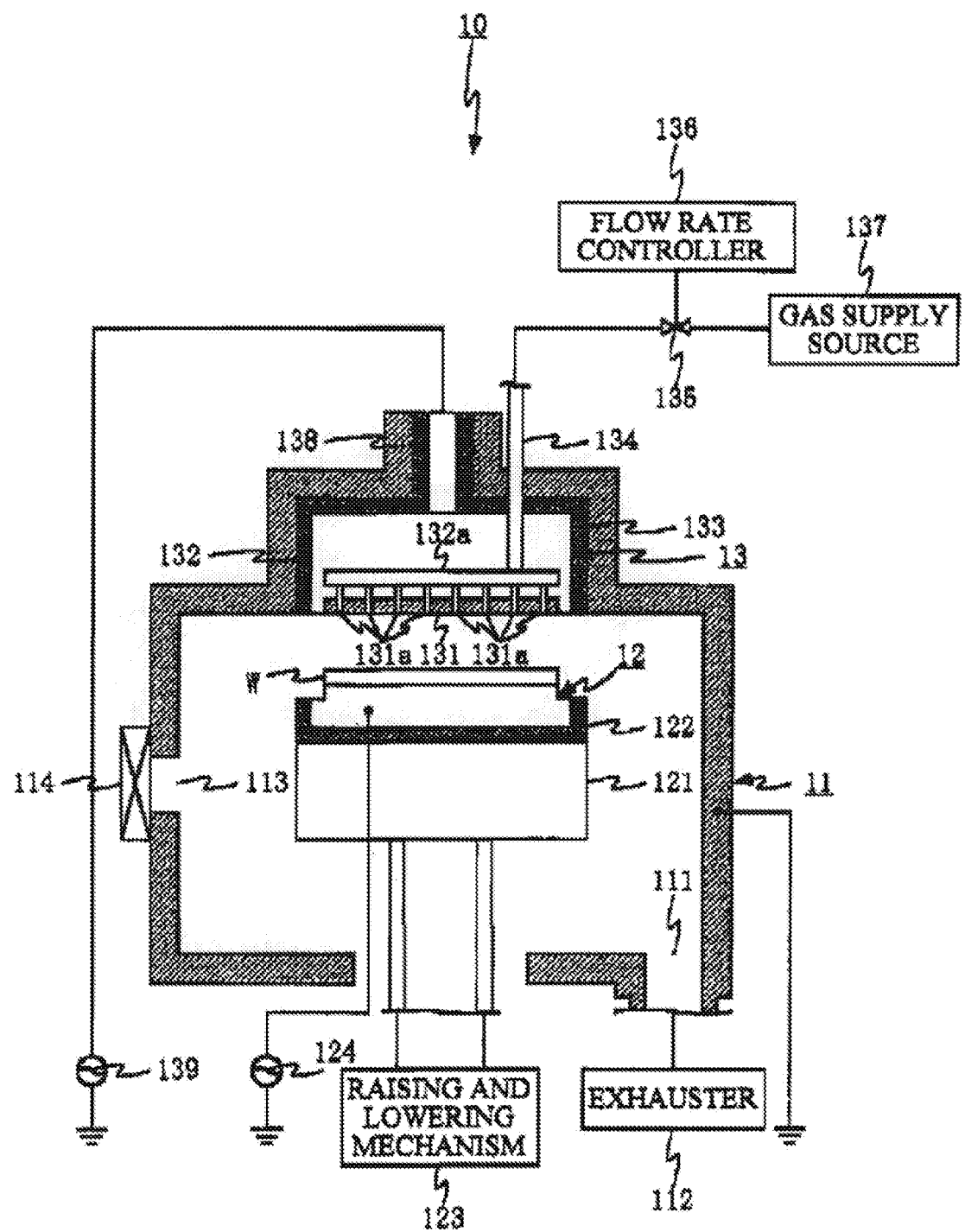
FIG. 2 is a diagram showing the configuration of a reduced-pressure processing apparatus according to the embodiment of the present invention.

The reduced-pressure processing apparatus 10, as shown in FIG. 2, is a so-called parallel plate type plasma processing apparatus comprising opposing electrodes vertically parallel to each other, and is roughly composed of an almost cylindrical chamber 11, a susceptor 12 which functions as a lower electrode, and an upper electrode 13. The reduced-pressure processing apparatus 10 selectively performs an etching processing for the wafer W using a resist pattern as a mask under a reduced-pressure atmosphere.

The chamber 11 is made of a conductive material such as aluminum or the like, and its surface has been subjected to anodizing such as an alumite treatment or the like. Further, the chamber 11 is grounded.

The chamber 11 includes an exhaust port 111 at its bottom portion, and the exhaust port 111 is connected with an exhauster 112 including a vacuum pump. The exhauster 112 can evacuate the chamber 11 to a predetermined reduced-pressure atmosphere, for example, a pressure of 0.01 Pa or lower.

The chamber 11 includes a carry in/out port 113 at its side wall. The carry in/out port 113 includes a gate valve 114 capable of opening and closing so that the gate valve 114 is opened to allow the wafer W to be carried in/out.

Further, an almost column-shaped susceptor supporting table 121 is provided at the center of the bottom portion in the chamber 11, and further a later-described susceptor 12 which functions as a wafer mounting table is provided on the susceptor supporting table 121 via an insulator 122. The susceptor supporting table 121 is connected to a raising and lowering mechanism 123 provided below the chamber 11 so as to be ascendable and descendable together with the susceptor 12.

The susceptor 12 is formed in a disc shape with its center of the upper portion projecting, on which a not-shown electrostatic chuck in almost the same shape as the wafer W is provided. When direct current is applied to this electrostatic chuck, the mounted wafer W is electrostatically attracted to the susceptor 12 by Coulomb force.

To the susceptor 12, a first high-frequency power source 124 is connected via a not-shown matching device. The first high-frequency power source 124 applies a high frequency (0.1 MHz to 13 MHz) voltage to the susceptor 12. By applying such a high frequency voltage, an effect of reducing the damage to the wafer W and so on is obtained.

The upper electrode 13, which is provided opposed to the susceptor 12, is composed of an electrode plate 131 and an electrode supporter 132 and supported on the upper portion of the chamber 11 via an insulator 133.

The electrode plate 131 is made of, for example, aluminum or the like and includes many gas holes 131a over almost the entire face.

The electrode supporter 132 is electrically connected to the electrode plate 131 with screws or the like and made of a conductive material. Besides, the electrode supporter 132 includes a gas introduction pipe 134 to which an etching gas composed of $C_4F_8$, argon, and oxygen is supplied from a gas supply source 137 through a valve 135, a flow rate controller 136 and so on. The electrode supporter 132 includes therein a hollow diffusion part 132a connected to the plurality of gas holes 131a of the electrode plate 131. The etching gas supplied from the gas supply source 137 through the gas introduction pipe 134 is diffused in the diffusion part 132a and then supplied to the gas holes 131a. This allows the etching gas to be evenly supplied to the entire surface of the wafer W from the plurality of gas holes 131a.

To the upper electrode 13, a feeding rod 138 made of a conductive material such as aluminum or the like is connected, and the feeding rod 138 is connected to a second high-frequency power source 139 via a not-shown matching device. The second high-frequency power source 139 supplies a high frequency (13 MHz to 150 MHz) power to the upper electrode 13. This generates high density plasma between the upper electrodes 13 and the susceptor 12 that is the lower electrode.

Figure 3:
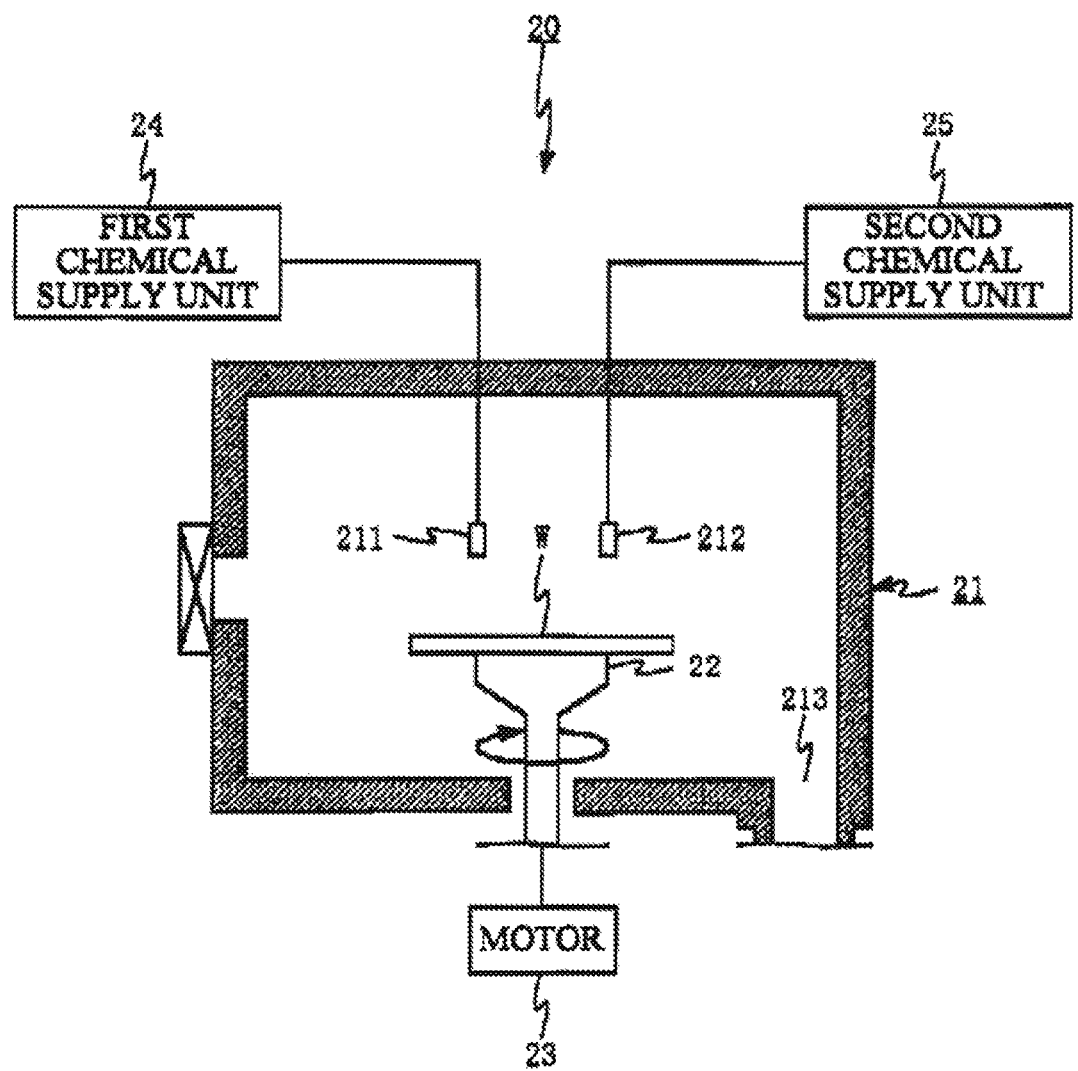
FIG. 3 is a diagram showing the configuration of a solution treatment apparatus according to the embodiment of the present invention.

The solution treatment apparatus 20 is a spinner type processing apparatus and roughly composed of, as shown in FIG. 3, an almost cylindrical chamber 21, a spin chuck 22 provided inside the chamber 21, a motor 23, a first chemical supply unit 24 which supplies a polymer removing solution and a resist layer removing solution to the surface of the wafer W, and a second chemical supply unit 25 which supplies pure water or isopropyl alcohol (IPA) for use in rinsing to the wafer W. The solution treatment apparatus 20 removes an unnecessary portion such as a polymer 8 attached to the surface of the wafer W, the resist layer 6, and so on, rinses the wafer W from which the polymer 8 and the resist layer 6 have been removed, and dries by spin the rinsed wafer W.

In the upper part of the chamber 21, a first chemical discharge nozzle 211 which is connected to the first chemical supply unit 24 to discharge the polymer removing solution and resist layer removing solution composed of, for example, hydrofluoric acid (HF) or sulfuric acid ($H_2SO_4$) to the surface of the wafer W, and a second chemical discharge nozzle 212 which is connected to the second chemical supply unit 25 to discharge the pure water or the like for use in rinsing to the surface of the wafer W, are provided. Further, in the lower part of the chamber 21, a drain port 213 is provided which drains the chemicals, the pure water, and so on discharged into the chamber 21.

The spin chuck 22 sucks the wafer W mounted thereon with vacuum, and the motor 23 rotates the wafer W sucked with vacuum by the spin chuck 22 at a high speed. The wafer W is rotated at a high speed by the motor 23, so that the centrifugal force generated by the rotation is utilized to evenly spread the discharged chemical, pure water, or the like over the surface of the wafer W. Further, the wafer W is rotated at a higher speed, whereby the rinsed wafer W is dried by spin.

Figure 4:
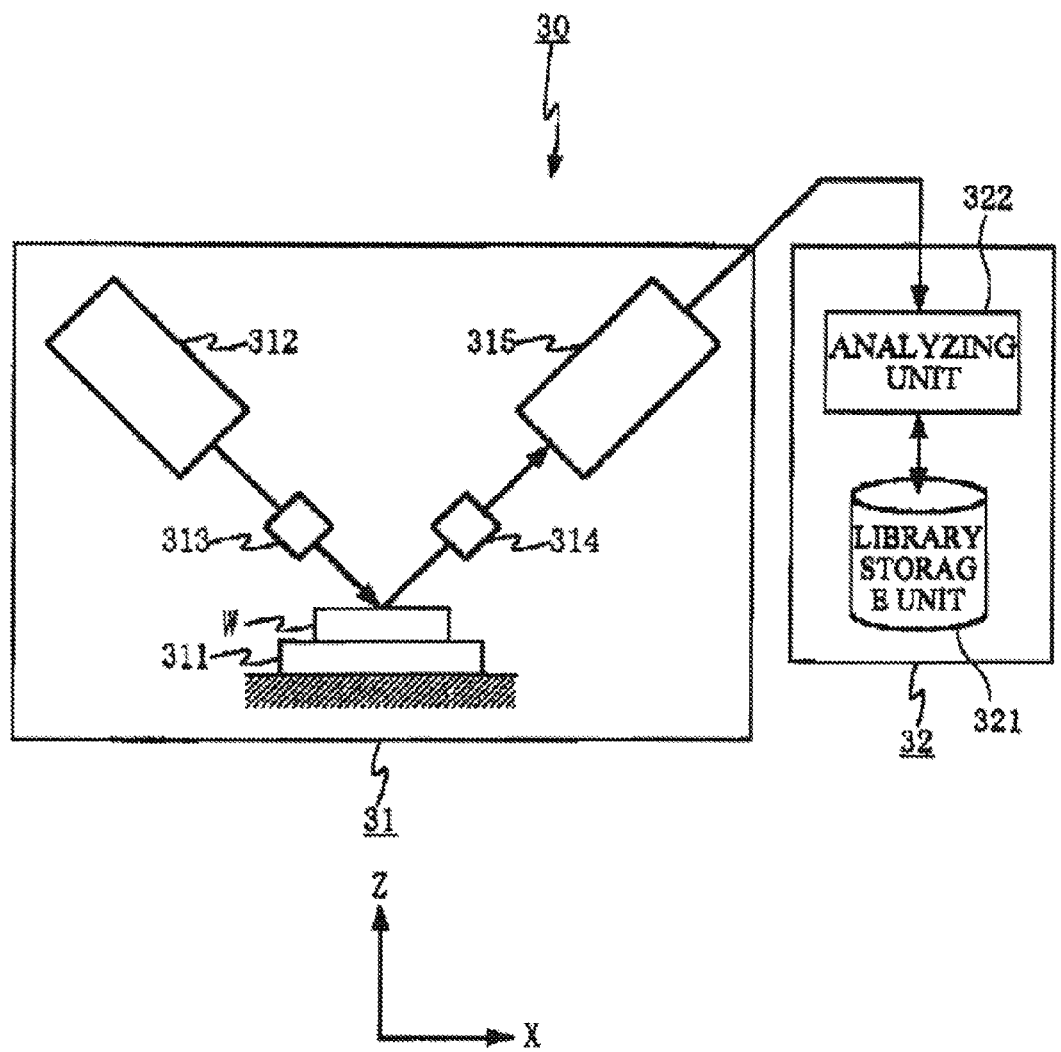
FIG. 4 is a diagram showing the configuration of a structure determination apparatus according to the first and third embodiments of the present invention.

The structure determination apparatus 30, as shown in FIG. 4, is composed of an optical unit 31 which applies polarized light to the wafer W and receives the polarized light reflected from the wafer W and a structure determination unit 32 which determines the surface structure of the wafer W from the reflected light, and determines the surface structure of the wafer W by Ellipsometry.

The Ellipsometry is a determination method of applying polarized light to the wafer W to determine the surface structure of the wafer W from a phase difference $\Delta$ and an amplitude displacement $\Psi$ between linearly polarized light applied to the wafer W and polarized light reflected from the wafer W. The phase shift and amplitude displacement $\Psi$ are defined by the following equations.

$$\Delta = (Wp - Ws)_{reflected\ light} - (Wp - Ws)_{incident\ light} \quad \text{(Equation 1)}$$

(Wp represents the phase of p component wave and Ws represents the phase of s component wave)

$$\Psi = \tan^{-1}\left[\frac{Rp}{Rs}\right], \quad \text{(Equation 2)}$$

$$Rp = (I_{reflected\ light} / I_{incident\ light})p,$$

$$Rs = (I_{reflected\ light} / I_{incident\ light})s$$

(Ip represents the intensity of p component wave, Is represents the intensity of s component wave, Rp represents the reflectance of p component wave, and Rs represents the reflectance of s component wave)

The optical unit 31 is composed of a mounting table 311, a light emitter 312, a polarizer 313, an analyzer 314, and a light receiver 315, and applies polarized light to the wafer W and receives the polarized light reflected from the wafer W.

The mounting table 311 is configured to be able to mount the wafer W thereon and be movable in an X-Y direction by a not-shown driving mechanism.

The light emitter 312 is composed of a xenon lamp or the like and emits white light toward the wafer W, and the polarizer 313 converts the white light emitted from the light emitter 312 into linearly polarized light and applies the converted linearly polarized light to the wafer W.

The analyzer 314 transmits only a polarized light component at a predetermined polarization angle out of elliptically polarized light reflected by the wafer W. The light receiver 315, which is composed of, for example, a CCD (Charge Coupled Device) camera or the like, receives the polarized light transmitted through the analyzer 314, converts the received light into an electrical signal, and supplies the converted electrical signal to the structure determination unit 32.

The structure determination unit 32 is composed of a library storage unit 321 and an analyzing unit 322, and estimates the surface structure of the wafer W from a phase difference $\Delta$ and an amplitude displacement $\Psi$ between the polarized light applied to the wafer W and the polarized light reflected from the wafer W.

The library storage unit 321, which is composed of a rewritable storage medium such as a hard disc drive or the like, stores a library in which a plurality of structure parameters representing the surface structures of the wafer W and phase difference distributions and amplitude displacement distributions are registered in an association manner.

Figure 5:
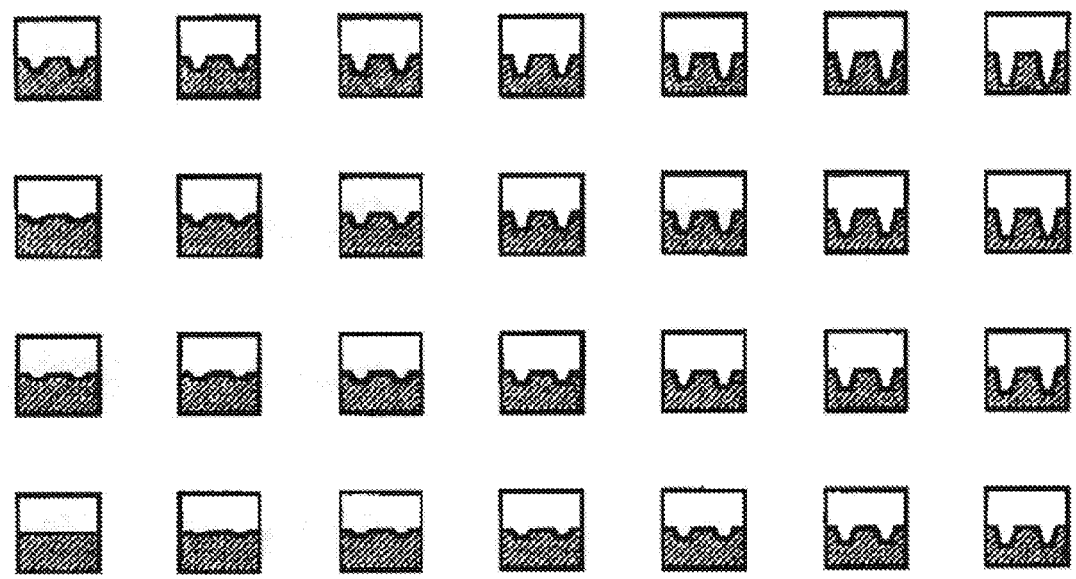
FIG. 5 is a view showing structure parameters registered, arranged in a matrix form, in a library stored in a library storage unit according to the first and third embodiments of the present invention.

In the library, as shown in FIG. 5, a plurality of structure parameters are registered, arranged in a matrix form. Further, in the library, in addition to the structure parameters arranged in a matrix form, a graph showing the cosine of the phase difference, cos $\Delta$ (phase difference distribution), at each wavelength $\lambda$, and a graph showing the tangent of the amplitude displacement, tan $\Psi$ (amplitude displacement distribution), at each wavelength $\lambda$, which have been previously calculated for the surface structure of the wafer W having the structure parameters, are registered as shown in FIG. 6.

The analyzing unit 322 is composed of a CPU, a RAM, a ROM, and so on. The analyzing unit 322 analyzes phases Wp reflected light and Ws reflected light and intensities Ip reflected light and Is reflected light at each wavelength $\lambda$, of the reflected light based on the electrical signal supplied from the optical unit 31. Further, the analyzing unit 322 calculates the phase difference $\Delta$ and the amplitude displacement $\Psi$ from phases Wp incident light and Ws incident light and intensities Ip incident light and Is incident light at each wavelength $\lambda$ of the light applied to the wafer W and the analyzed phases Wp reflected light and Ws reflected light and intensities Ip reflected light and Is reflected light at each wavelength $\lambda$ of the reflected light through use of Equation 1 and Equation 2, so as to find the phase difference distribution and the amplitude displacement distribution.

Figure 7:
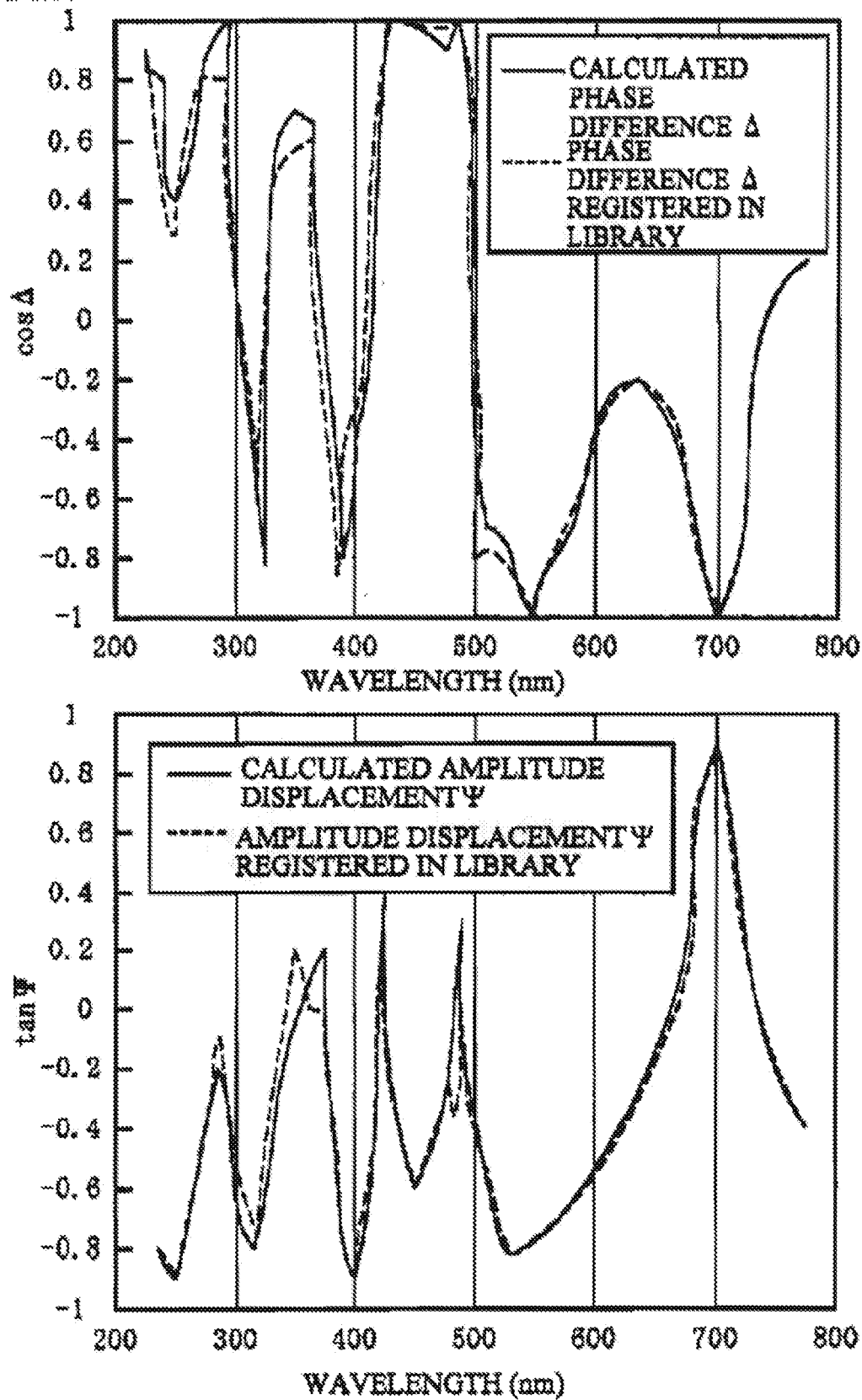
FIG. 7 is an explanatory view of an operation of an analyzing unit according to the first and third embodiments of the present invention of performing pattern matching of a calculated phase difference Δ and amplitude displacement Ψ to the library.

The analyzing unit 322, as shown in FIG. 7, performs pattern matching of the found phase difference distribution and amplitude displacement distribution to each of the phase difference distributions and amplitude displacement distributions registered in the library to retrieve from the library phase difference distributions and amplitude displacement distributions which are approximate to the found phase difference distribution and amplitude displacement distribution.

The analyzing unit 322 corrects, using an interpolation method, the structure parameters corresponding to the retrieved phase difference distributions and amplitude displacement distributions in accordance with the rate of approximation of the found phase difference distribution and amplitude displacement distribution to the phase difference distributions and amplitude displacement distributions retrieved from the library, and estimates the surface structure of the wafer W from the corrected structure parameter.

Figure 8:
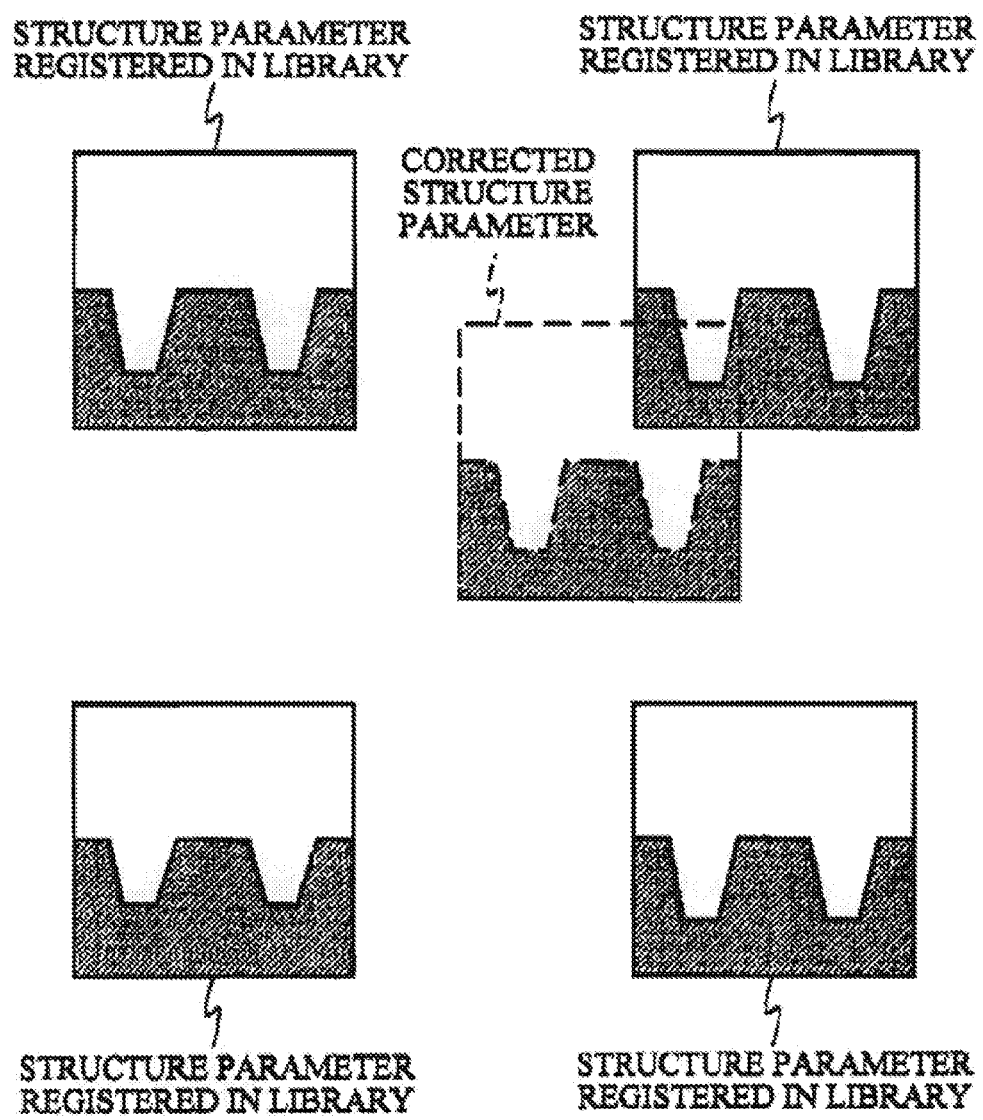
FIG. 8 is an explanatory view of an operation of the analyzing unit according to the first and third embodiments of the present invention of correcting the structure parameter, and estimating and determining the surface structure of the wafer W.

To described in more detail, the analyzing unit 322 retrieves from the library as shown in FIG. 8 four phase difference distributions and amplitude displacement distributions approximate to the found phase difference distribution and amplitude displacement distribution, composites the structure parameters corresponding to the four phase difference distributions and amplitude displacement distributions retrieved in accordance with the rate of approximation of the found phase difference distribution and amplitude displacement distribution to the retrieved phase difference distributions and amplitude displacement distributions, and estimates the surface structure of the wafer W from the structure parameter resulting from the composition.

The system control apparatus 40 shown in FIG. 1 is composed of a CPU, a RAM, a ROM, and so on. The system control apparatus 40 controls the carrier mechanism 60 to carry the wafer W out of the load port 50 and carry the carried-out wafer W to the alignment unit 70, the reduced-pressure processing apparatus 10, and so on. The system control apparatus 40 carries the wafer W, which has been subjected to predetermined processing in each of the apparatuses 10 to 30, into the load port 50.

Figure 9:
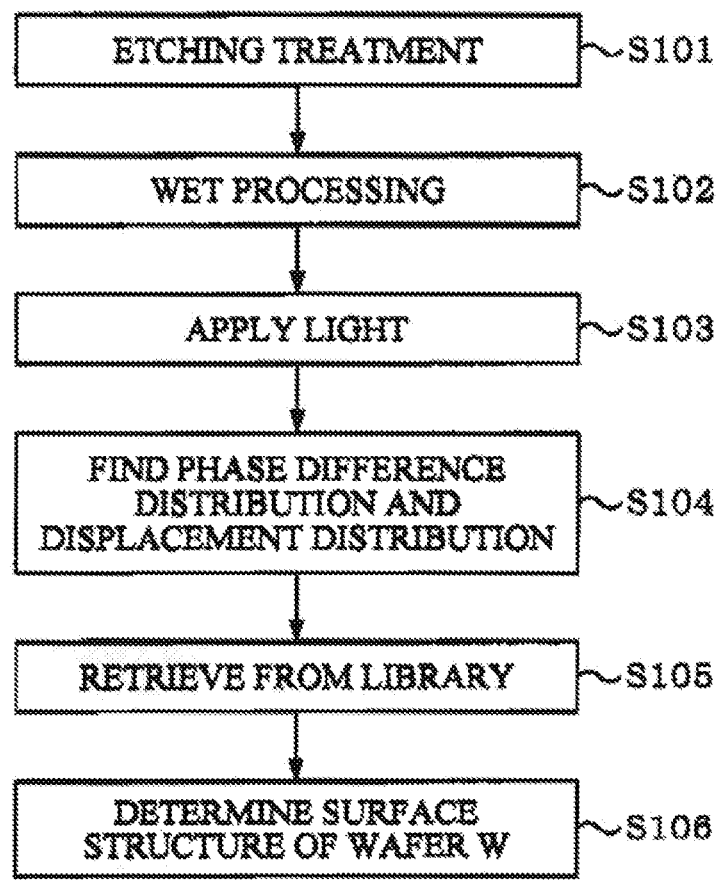
FIG. 9 is a flowchart showing a processing operation according to the first embodiment of the present invention.
Figure 10A:
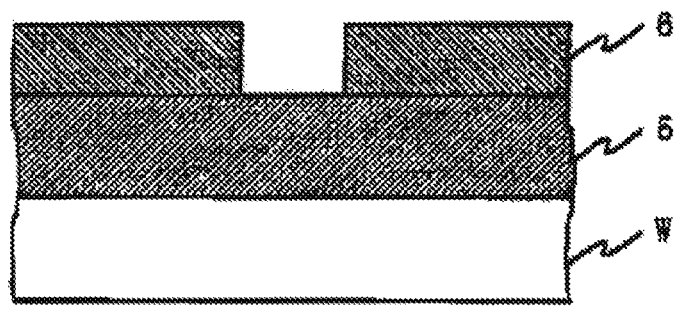
FIGS. 10A to 10C are cross-sectional views showing the structure of the wafer in steps of the processing operation according to the first embodiment of the present invention.
Figure 10B:
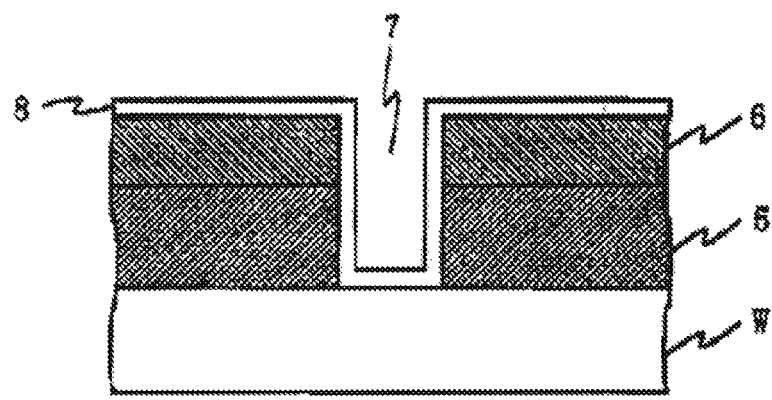
Figure 10C:
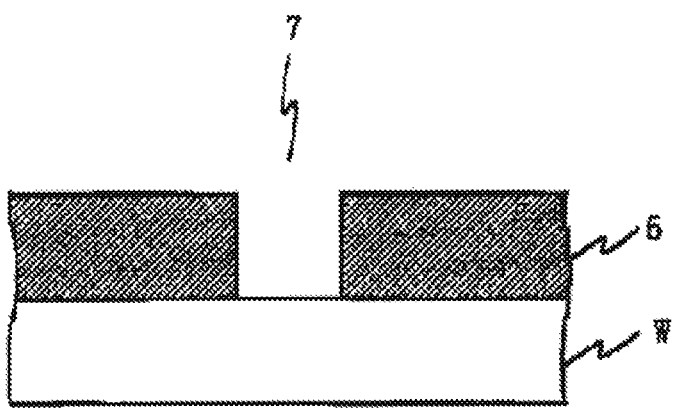

Next, referring to a flowchart shown in FIG. 9 and cross-sectional views of the wafer W in steps shown in FIGS. 10A to 10C, the processing operation of the processing system 1 will be described taking as an example a case in which a plurality of contact holes are formed in a wafer W and the surface structure of the wafer W formed with the contact holes is determined.

First, the wafer W is carried to a not-shown oxidizing apparatus. The oxidizing apparatus performs an oxidation treatment to form the $SiO_2$ layer 5 within the surface region of the wafer W.

Then, the wafer W formed with the $SiO_2$ layer 5 within the surface region is carried to a not-shown resist coating apparatus. The resist coating apparatus applies a resist onto the $SiO_2$ layer 5. Subsequently, the wafer W coated with the resist is carried to a not-shown aligner. The aligner performs exposure processing for the resist applied on the surface of the wafer W. Subsequently, the wafer W subjected to the exposure processing is carried to a not-shown developing apparatus. The developing apparatus performs a developing treatment for the resist applied on the surface of the wafer W to form a resist pattern for forming the contact hole shown in FIG. 10A. Thereafter, the wafer W having the resist pattern formed on the surface is carried out of the developing apparatus.

The system control apparatus 40 controls the carrier mechanism 60 to carry the wafer W housed in the load port 50 to the alignment unit 70, which aligns the wafer W. Then, the gate valve 114 of the carry in/out port 113 is opened, and the system control apparatus 40 carries the wafer W, which has been carried out of the developing apparatus, into the chamber 11 of the reduced-pressure processing apparatus 10 and mounts the carried-in wafer W on the susceptor 12. Thereafter, the system control apparatus 40 retracts the carrier mechanism 60 from the inside of the chamber 11 and closes the gate valve 114. The reduced-pressure processing apparatus 10 drives the raising and lowering mechanism 123 to raise the susceptor 12 with the wafer W mounted thereon together with the susceptor supporting table 121 to a predetermined position. The reduced-pressure processing apparatus 10 evacuates the chamber 11 using the exhauster 112 to a predetermined reduced-pressure atmosphere, for example, a pressure of 0.01 Pa and lower. The reduced-pressure processing apparatus 10 applies direct current to the electrostatic chuck provided on the susceptor 12 to electrostatically attract the wafer W to the susceptor 12.

The reduced-pressure processing apparatus 10 opens the valve 135 of the gas introduction pipe 134 to diffuse the etching gas composed of $C_4F_8$, argon, and oxygen supplied from the gas supply source 137 in the diffusion part 132$a$, and then introduces it into the chamber 11 through the gas holes 131$a$. The reduced-pressure processing apparatus 10 applies a high-frequency voltage of 0.1 MHz to 13 MHz to the susceptor 12 and a high-frequency voltage of 13 MHz to 150 MHz to the upper electrode 13 so as to generate a high density plasma gas between the susceptor 12 and the upper electrode 13. The reduced-pressure processing apparatus 10 selectively etches the surface of the wafer W using the generated plasma gas with the resist pattern as a mask (Step S101). This etching processing forms a contact hole 7 shown in FIG. 10B in the $SiO_2$ layer 5 on the wafer W and causes a polymer 8 to attach to the surfaces of the resist layer 6 and the contact hole 7.

After completion of the etching processing, the reduced-pressure processing apparatus 10 stops the application of the high-frequency voltages to the susceptor 12 and the upper electrode 13 and closes the valve 135 of the gas introduction pipe 134. Further, the reduced-pressure processing apparatus 10 stops the application of the direct current to the susceptor 12 and returns the inside of the chamber 11 to a normal-pressure atmosphere. Further, the reduced-pressure processing apparatus 10 drives the raising and lowering mechanism 123 to lower the susceptor 12 with the wafer W mounted thereon together with the susceptor supporting table 121 to a predetermined position. The system control apparatus 40 opens the gate valve 114, carries the wafer W with the polymer 8 attached thereto out of the reduced-pressure processing apparatus 10, and closes the gate valve 114 after the carrying out. The system control apparatus 40 carries the wafer W, which has been carried out of the reduced-pressure processing apparatus 10, into the chamber 21 of the solution treatment apparatus 20, and mounts the carried-in wafer W on the spin chuck 22.

The solution treatment apparatus 20 sucks the mounted wafer W onto the spin chuck 22 with vacuum and rotates the wafer W sucked with vacuum by the motor 23. The solution treatment apparatus 20 discharges the polymer removing solution and resist layer removing solution composed of, for example, hydrofluoric acid (HF) or sulfuric acid ($H_2SO_4$), which are supplied from the first chemical supply unit 24, from the first chemical discharge nozzle 211 onto the surface of the wafer W which is being rotated by the motor 23. The solution treatment apparatus 20 utilizes the centrifugal force generated by the rotation to evenly spread the discharged polymer removing solution and resist layer removing solution over the surface of the wafer W, thereby removing the polymer 8 and the resist layer 6 on the surface of the wafer W as shown in FIG. 10C (Step S102).

The solution treatment apparatus 20 discharges the pure water or IPA solution, which is supplied from the second chemical supply unit 25, from the second chemical discharge nozzle 212 onto the surface of the wafer W which is being rotated by the motor 23. The solution treatment apparatus 20 utilizes the centrifugal force generated by the rotation to evenly spread the discharged pure water or IPA solution over the surface of the wafer W, thereby rinsing the surface of the wafer W from which the polymer 8 and the resist layer 6 have been removed. The solution treatment apparatus 20 allows the motor 23 to rotate the wafer W at a higher speed to dry by spin the rinsed wafer W. The system control apparatus 40 carries the wafer W from which the polymer 8 and the resist layer 6 have been removed into the structure determination apparatus 30 and mounts the carried-in wafer W on the mounting table 311 of the structure determination apparatus 30.

The optical unit 31 emits white light from the light emitter 312 toward the wafer W, converts the white light into linearly polarized light by the polarizer 313, and applies the converted linearly polarized light to the wafer W (Step S103). The optical unit 31 receives at the light receiver 315 the polarized light reflected by the wafer W and transmitted through the analyzer 314, converts the received polarized light into an electrical signal, and supplies the converted electrical signal to the structure determination unit 32.

The structure determination unit 32 analyzes reflected light with a phase of Wp and reflected light with a phase of Ws and reflected light with an intensity of Ip and reflected light with an intensity of Is at each wavelength $\lambda$ of the reflected light based on the supplied electrical signal. Further, the structure determination unit 32 calculates the phase difference $\Delta$ and the amplitude displacement $\Psi$ from phases Wp incident light and Ws incident light and intensities Ip incident light and Is incident light at each wavelength $\lambda$ of the light applied to the wafer W and the analyzed phases Wp reflected light and Ws reflected light and intensities Ip reflected light and Is reflected light at each wavelength $\lambda$ of the reflected light through use of Equation 1 and Equation 2, so as to find the phase difference distribution and the amplitude displacement distribution (Step S104).

The structure determination unit 32 performs pattern matching of the found phase difference distribution and amplitude displacement distribution to each of the phase difference distributions and amplitude displacement distributions registered in the library to retrieve from the library a phase difference distribution and an amplitude displacement distribution which are approximate to the calculated phase difference distribution and amplitude displacement distribution (Step S105).

The structure determination unit 32 retrieves from the library four phase difference distributions and amplitude displacement distributions which are approximate to the found phase difference distribution and amplitude displacement distribution, composites the structure parameters corresponding to the four phase difference distributions and amplitude displacement distributions in accordance with the rate of approximation of the found phase difference distribution and amplitude displacement distribution to the retrieved phase difference distributions and amplitude displacement distributions, and estimates the surface structure of the wafer W from the structure parameter resulting from the composition (Step S106).

According to the above-described processing operation, the polymer 8 having unclear shape and composition is removed, so that the processing system 1 can specify the optical constant n value (refractive index) and the k value (absorption coefficient) on the surface of the wafer W to accurately nondestructively determine by Ellipsometry the surface structure of the wafer W.

Second Embodiment

A processing system 2 according to a second embodiment of the present invention will be described below with reference to the drawings. Note that the description of the same configuration as that of the processing system 1 according to the above-described first embodiment will be omitted.

Figure 11:
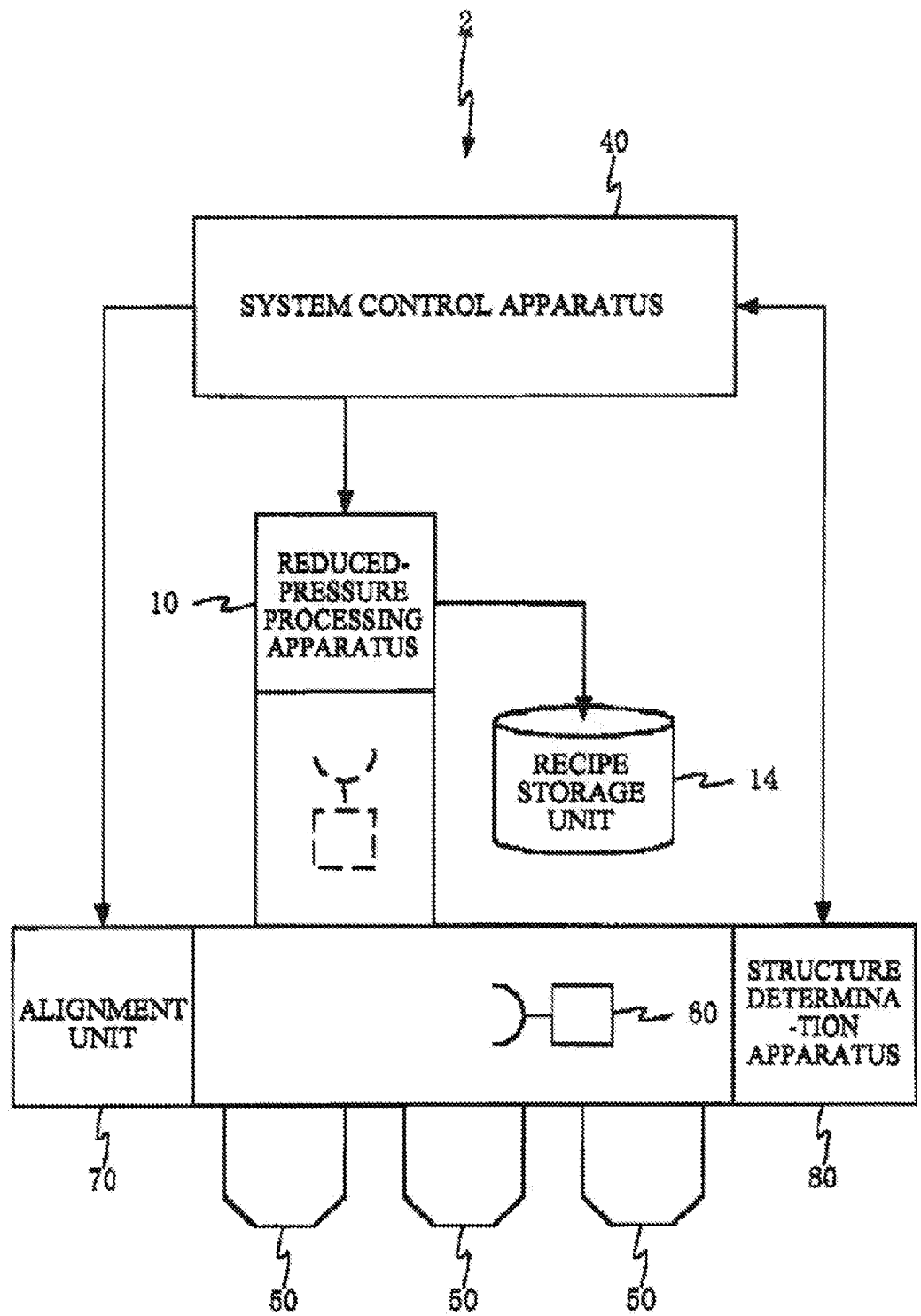
FIG. 11 is a diagram showing the configuration of a processing system according to a second embodiment of the present invention.

The processing system 2, as shown in FIG. 11, is composed of a reduced-pressure processing apparatus 10, a recipe storage unit 14, a structure determination apparatus 80, a system control apparatus 40, load ports 50, a carrier mechanism 60, and an alignment unit 70, performs an etching processing for a wafer that is a workplace, and determines by Reflectometry the surface structure of the wafer W after the etching processing.

The reduced-pressure processing apparatus 10 selectively performs an etching processing for the wafer W with a resist pattern as a mask under a reduced-pressure atmosphere. Further, the reduced-pressure processing apparatus 10 removes by in situ aching processing unnecessary portions such as a deteriorated layer and/or a hard layer (deteriorated hard layer) formed in a resist layer and a damaged layer formed within the bottom region of a contact hole and so on in the etching processing. Note that the reduced-pressure processing apparatus 10 uses $CF_4$ as the etching gas and $O_2$ as the ashing gas.

Here, the resist layer deteriorated in shape and composition due to heat of plasma and incident energy and so on in the etching processing is referred to as a deteriorated layer, the resist layer hardened is referred to as a hard layer, and the surface of the wafer W deteriorated in shape and composition is referred to as a damaged layer. Besides, the reason why not all of the resist layer is removed, but only the deteriorated hard layer formed in the resist layer is removed by the etching processing to leave the resist layer in the in situ ashing processing is as follows. Namely, in recent years, with higher integration of the semiconductor integrated circuit, such a lithography technique is desired that is employed on a semiconductor substrate with a higher step and a higher reflection, which requires resist layers stacked in two or three layers for use in processing fine patterns, and therefore the resist layer is left. It should be noted that the technique is described in, for example, Japanese Patent Application Laid-open No. Hei 5-160014 and so on.

A flow rate controller 136 is composed of a CPU, a ROM, and so on, and includes therein a not-shown memory composed of a RAM or the like and a not-shown clock circuit. The flow rate controller 136 selects an optimal recipe from the recipe storage unit 14 based on the surface structure of the wafer W designated by a not-shown input unit and stores an etching condition (for example, Gr) registered in the selected optimal recipe into the memory to thereby (initially) set the etching condition. Further, the flow rate controller 136 supplies the structure parameter representing the surface structure of the wafer W designated by the input unit and the (initially) set etching condition (Gr) to the later-described system control apparatus 40.

The flow rate controller 136 supplies a set flow rate of etching gas into a chamber 11 by adjusting the open time of a valve 135 using the clock circuit. Further, when an etching condition (for example, Gr+ΔG) is supplied from the system control apparatus 40, the flow rate controller 136 rewrites the etching condition stored in the memory from (Gr) to (Gr+ΔG) to thereby change the setting of the etching condition.

The recipe storage unit 14, which is composed of a rewritable storage medium such as a hard disc drive or the like, stores a plurality of recipes in which the etching condition composed of a gas flow rate G to be supplied to the chamber 11 is registered.

Figure 12:
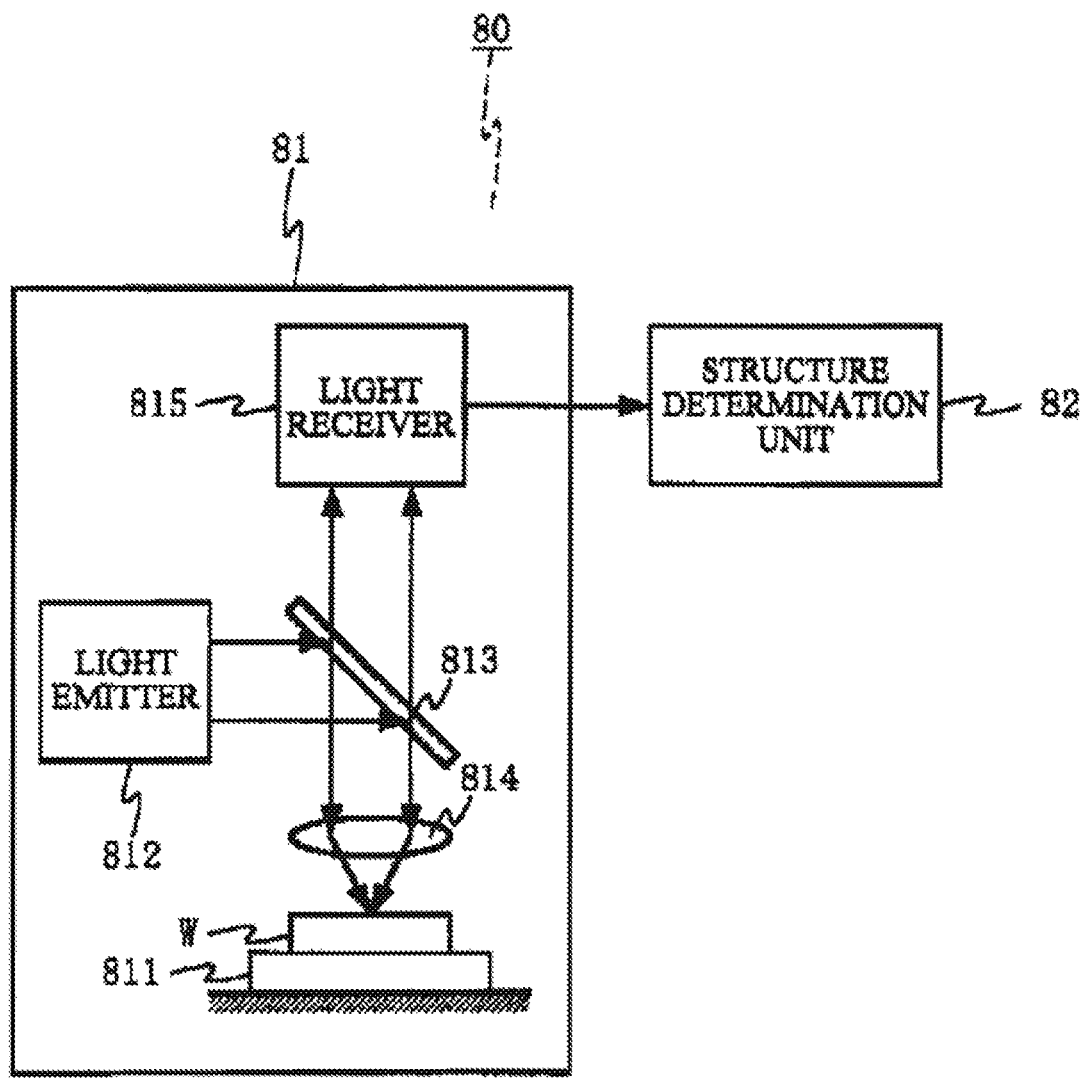
FIG. 12 is a diagram showing the configuration of a structure determination apparatus according to the second and a fourth embodiment of the present invention.

The structure determination apparatus 80 is composed of, as shown in FIG. 12, an optical unit 81 which applies light to the wafer W and receives reflected light from the wafer W and a structure determination unit 82 which determines the surface structure of the wafer W based on the reflected light, and determines the surface structure of the wafer W by Reflectometry.

This Reflectometry is a determining method of applying light to the wafer W to determine the surface structure of the wafer W from the ratio of the intensity of the light applied to the wafer W to the intensity of the light reflected from the wafer W (reflectance).

The optical unit 81 is composed of a mounting table 811, a light emitter 812, a reflecting mirror 813, a lens 814, and a light receiver 815 and applies light to the wafer W and receives reflected light from the wafer W.

The mounting table 811 is configured to be able to mount the wafer W thereon and be movable in an XY direction by a not-shown driving mechanism.

The light emitter 812 emits white light to be applied to the wafer W horizontally with respect to the surface of the ground. The reflecting mirror 813 is made of glass or the like and reflects the white light emitted from the light emitter 812 horizontally with respect to the surface of the ground to apply the reflected white light to the wafer W at a vertically lower position. The lens 814 is made of glass or the like and condenses the white light made incident from the reflecting mirror 813 to the surface of the wafer W mounted on the mounting table 811.

The light receiver 815 receives the reflected light from the wafer W, converts the received reflected light into an electrical signal, and supplies the converted electrical signal to the structure determination unit 82.

The structure determination unit 82, is composed of a CPU, a RAM, a ROM, and so on and estimates the surface structure of the wafer W from the ratio of the intensity of the light applied to the wafer W to the intensity of the light reflected from the wafer W (reflectance). Further, the structure determination unit 82 stores in the ROM a predetermined multiple regression equation capable of calculating the structure parameter by multiple regression analysis using the reflectance as a variable.

The structure determination unit 82 analyzes an intensity I reflected light at each wavelength λ of the reflected light based on the electrical signal supplied from the optical unit 81. Further, the structure determination unit 82 calculates the reflectance (=I reflected light/I incident light) from the an intensity I incident light at each wavelength λ of the light applied to the wafer W and the analyzed intensity I reflected light at each wavelength λ of the reflected light.

The structure determination unit 82 carries out multiple regression analysis using the calculated reflectance (=I reflected light/I incident light) and the predetermined multiple regression equation stored in the ROM to calculate the structure parameter so as to estimate the surface structure of the wafer W from the calculated structure parameter. The structure determination unit 82 supplies the calculated structure parameter to the system control apparatus 40.

The system control apparatus 40 is supplied with the structure parameter representing the surface structure of the wafer W designated in the reduced-pressure processing apparatus 10 and the (initially) set etching condition and stores the supplied structure parameter and etching condition into the memory.

The system control apparatus 40 compares the structure parameters stored in the memory to the structure parameter supplied from the structure determination unit 82 and corrects the etching condition stored in the memory based on the comparison result. The system control apparatus 40 supplies the corrected etching condition to the reduced-pressure processing apparatus 10, thereby feeding back the etching condition to the reduced-pressure processing apparatus 10.

Where a plurality of contact holes, for example, are formed in the wafer W, the system control apparatus 40 compares the structure parameter stored in the memory to the structure parameter supplied from the structure determination unit 82, thereby comparing the depth of the contact hole or the like designated in the reduced-pressure processing apparatus 10 to the depth or the like of the actually formed contact hole.

When the depth of the actually formed contact hole is shallower than the depth of the designated contact hole, the system control apparatus 40 corrects the (initially) set etching condition Gr to Gr+ΔG so as to increase the gas flow rate to be supplied to the chamber 11. The system control apparatus 40 supplies the corrected etching condition (Gr+ΔG) to the reduced-pressure processing apparatus 10.

Figure 14A:
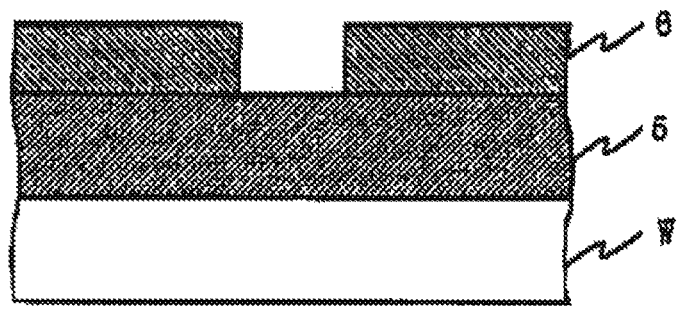
FIGS. 14A to 14C are cross-sectional views showing the structure of the wafer in steps of the processing operation according to the second embodiment of the present invention.
Figure 14B:
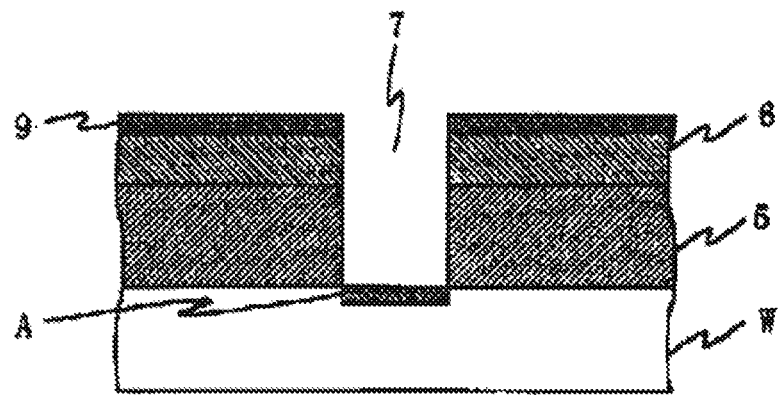
Figure 14C:
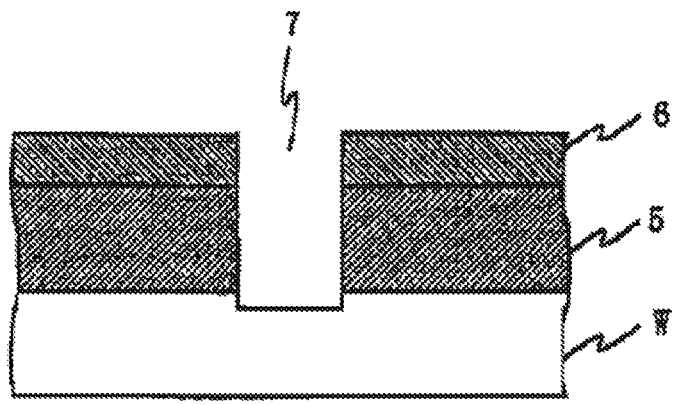

Next, referring to a flowchart shown in FIG. 13 and cross-sectional views of the wafer W in steps shown in FIGS. 14A to 14C, the processing operation of the processing system 2 will be described taking as an example a case in which a plurality of contact holes are formed in a wafer W and the surface structure of the wafer W formed with the contact holes is determined to feed back the etching condition.

First, the wafer W is carried to a not-shown oxidizing apparatus. The oxidizing apparatus performs an oxidation treatment to form a $SiO_2$ layer 5 within the surface region of the wafer W.

Then, the wafer W formed with the $SiO_2$ layer 5 within the surface region is carried to a not-shown resist coating apparatus. The resist coating apparatus applies a resist onto the $SiO_2$ layer 5. Subsequently, the wafer W coated with the resist is carried to a not-shown aligner. The aligner performs exposure processing for the resist applied on the surface of the wafer W. Subsequently, the wafer W subjected to the exposure processing is carried to a not-shown developing apparatus. The developing apparatus performs a developing treatment for the resist applied on the surface of the wafer W to form a resist pattern for forming the contact hole shown in FIG. 14A. Thereafter, the wafer W having the resist pattern formed on the surface is carried out of the developing apparatus.

The system control apparatus 40 controls the carrier mechanism 60 to carry the wafer W housed in the load port 50 to the alignment unit 70, which aligns the wafer W. Then, a gate valve 114 of a carry in/out port 113 is opened, and the system control apparatus 40 carries the wafer W, which has been carried out of the developing apparatus, into the chamber 11 of the reduced-pressure processing apparatus 10 and mounts the carried-in wafer W on a susceptor 12. Thereafter, the system control apparatus 40 retracts the carrier mechanism 60 from the inside of the chamber 11 and closes the gate valve 114. The reduced-pressure processing apparatus 10 drives a raising and lowering mechanism 123 to raise the susceptor 12 with the wafer W mounted thereon together with a susceptor supporting table 121 to a predetermined position.

The reduced-pressure processing apparatus 10 evacuates the chamber 11 using an exhauster 112 to a predetermined reduced-pressure atmosphere, for example, a pressure of 0.01 Pa and lower. The reduced-pressure processing apparatus 10 applies direct current to an electrostatic chuck provided on the susceptor 12 to electrostatically attract the wafer W to the susceptor 12.

The reduced-pressure processing apparatus 10 selects an optimal recipe from the recipe storage unit 14 based on the surface structure of the wafer W with a resist pattern for forming a plurality of contact holes designated by the input unit and stores the etching condition (Gr) registered in the selected optimal recipe into the memory to thereby (initially) set the etching condition (Step S201).

The reduced-pressure processing apparatus 10 supplies the structure parameter representing the surface structure of the wafer W designated by the input unit and the set etching condition (Gr) to the system control apparatus 40. The system control apparatus 40 stores the supplied structure parameter and (initially) set etching condition into the memory.

The reduced-pressure processing apparatus 10 opens, under the set etching condition (Gr), the valve 135 of the gas introduction pipe 134 to diffuse the etching gas composed of $CF_4$ supplied from the gas supply source 137 in a diffusion part 132a, and then introduces it into the chamber 11 through gas holes 131a. The reduced-pressure processing apparatus 10 applies high-frequency voltages to the susceptor 12 and an upper electrode 13 so as to generate a high density plasma gas between the susceptor 12 and the upper electrode 13. The reduced-pressure processing apparatus 10 selectively etches the surface of the wafer W using the generated plasma gas with the resist pattern as a mask (Step S202). This etching processing forms a contact hole 7 shown in FIG. 14B in the $SiO_2$ layer 5 on the wafer W and forms a deteriorated hard layer 9 on a resist layer 6 and a damaged layer A within the bottom region of the contact hole 7.

After completion of the etching processing, the reduced-pressure processing apparatus 10 stops the application of the high-frequency voltages to the susceptor 12 and the upper electrode 13 and closes the valve 135 of the gas introduction pipe 134. Further, the reduced-pressure processing apparatus 10 brings the inside the chamber 11 into an in situ ashing atmosphere.

The reduced-pressure processing apparatus 10 opens the valve 135 of the gas introduction pipe 134 to diffuse the ashing gas composed of $O_2$ supplied from a gas supply source 137 in the diffusion part 132a, and then introduces it into the chamber 11 through the gas holes 131a. The reduced-pressure processing apparatus 10 applies high-frequency voltages to the susceptor 12 and the upper electrode 13 so as to generate a high density plasma gas between the susceptor 12 and the upper electrode 13. The reduced-pressure processing apparatus 10 performs the in situ ashing processing for the wafer W using the generated plasma gas to thereby remove, as shown in FIG. 14C, the deteriorated hard layer 9 formed in the resist layer 6 and the damaged layer A formed within the bottom region of the contact hole 7 (Step S203).

After completion of the in situ ashing processing, the reduced-pressure processing apparatus 10 stops the application of the high-frequency voltages to the susceptor 12 and the upper electrode 13 and closes the valve 135 of the gas introduction pipe 134. Further, the reduced-pressure processing apparatus 10 stops the application of the direct current to the susceptor 12 and returns the inside of the chamber 11 to a normal-pressure atmosphere. Further, the reduced-pressure processing apparatus 10 drives the raising and lowering mechanism 123 to lower the susceptor 12 with the wafer W mounted thereon together with the susceptor supporting table 121 to a predetermined position. The system control apparatus 40 opens the gate valve 114, carries the wafer W, from which the deteriorated hard layer 9 and the damaged layer A have been removed, out of the reduced-pressure processing apparatus 10, and closes the gate valve 114 after the carrying out. The system control apparatus 40 carries the wafer W, which has been carried out of the reduced-pressure processing apparatus 10, into the structure determination apparatus 80 and mounts the carried-in wafer W on the mounting table 811.

The optical unit 81 emits white light from the light emitter 812 horizontally with respect to the surface of the ground, reflects the white light vertically downward by the reflecting mirror 813 to apply the reflected white light to the wafer W via the lens 814 (Step S204). The optical unit 81 receives reflected light from the wafer W, converts the received reflected light into an electrical signal, and supplies the converted electrical signal to the structure determination unit 82.

The structure determination unit 82 analyzes an intensity I reflected light at each wavelength λ of the reflected light based on the electrical signal supplied from the optical unit 81. Further, the structure determination unit 82 calculates the reflectance (=I reflected light/I incident light) from an intensity I incident light at each wavelength λ of the light applied to the wafer W and the analyzed intensity I reflected light at each wavelength λ of the reflected light (Step S205).

The structure determination unit 82 carries out multiple regression analysis using the calculated reflectance (=I reflected light/I incident light) and the predetermined multiple regression equation stored in the ROM to calculate the structure parameter (Step S206).

The structure determination unit 82 estimates the surface structure of the wafer W formed with the plurality of contact holes 7 from the calculated structure parameter (Step S207). The structure determination unit 82 supplies the calculated structure parameter to the system control apparatus 40.

The system control apparatus 40 compares the structure parameter stored in the memory to the structure parameter supplied from the structure determination unit 82, thereby comparing the depth of the contact hole or the like designated in the reduced-pressure processing apparatus 10 to the depth or the like of the actually formed contact hole (Step S208).

When the depth of the actually formed contact hole 7 is shallower than the depth of the designated contact hole, the system control apparatus 40 corrects the (initially) set etching condition Gr to Gr+ΔG so as to increase the gas flow rate to be supplied to the chamber 11 (Step S209). The system control apparatus 40 supplies the corrected etching condition (Gr+ΔG) to the reduced-pressure processing apparatus 10, thereby feeding back the etching condition to the reduced-pressure processing apparatus 10.

When the etching condition (Gr+ΔG) is supplied from the system control apparatus 40, the reduced-pressure processing apparatus 10 rewrites the etching condition stored in the memory from (Gr) to (Gr+ΔG) to thereby change the setting of the etching condition (Step S210).

According to the above-described processing operation, the deteriorated hard layer 9 and damaged layer A having unclear shapes and compositions are removed, so that the processing system 2 can specify the optical constant n value (refractive index) and the k value (absorption coefficient) on the surface of the wafer W to accurately nondestructively determine by Reflectometry the surface structure of the wafer W.

Further, the processing system 2 corrects the etching condition to be supplied to the reduced-pressure processing apparatus 10 from the surface structure of the wafer W which has been accurately determined by Reflectometry and feeds back the etching condition, whereby the processing system 2 can perform an accurate and uniform etching processing for the wafer W.

Third Embodiment

A processing system 3 according to a third embodiment of the present invention will be described below with reference to the drawings. Note that the description of the same configuration as that of the processing systems 1 and 2 according to the above-described first and second embodiments will be omitted.

The processing system 3, as in the processing system 1 shown in FIG. 1, is composed of a reduced-pressure processing apparatus 10, a solution treatment apparatus 20, a structure determination apparatus 30, a system control apparatus 40, load ports 50, a carrier mechanism 60, and an alignment unit 70, performs an etching processing for a wafer W that is a workpiece, and determines by Ellipsometry the surface structure of the wafer W after the etching processing.

The reduced-pressure processing apparatus 10 selectively performs an etching processing for the wafer W with a resist pattern as a mask under a reduced-pressure atmosphere. Further, the reduced-pressure processing apparatus 10 removes by in situ miring processing an unnecessary portion such as a polymer attached to the surface of the wafer W. Note that the reduced-pressure processing apparatus 10 uses a mixed gas composed of $C_4F_g$, argon, and oxygen as the etching gas and $O_2$ as the ashing gas.

The solution treatment apparatus 20 removes an unnecessary portion such as a resist layer or the like which has been significantly changed in shape and composition, rinses the wafer W from which a resist layer 6 has been removed, and dries by spin the rinsed wafer W.

The structure determination apparatus 30 is composed of an optical unit 31 and a structure determination unit 32, and determines the surface structure of the wafer W by Ellipsometry. The optical unit 31 is composed of a mounting table 311, a light emitter 312, a polarizer 313, an analyzer 314, and a light receiver 315, and applies polarized light to the wafer W and receives polarized light reflected from the wafer W.

The structure determination unit 32 is composed of a library storage unit 321 and an analyzing unit 322, and estimates the surface structure of the wafer W from a phase difference Δ and an amplitude displacement Ψ between the polarized light applied to the wafer W and the polarized light reflected from the wafer W.

The library storage unit 321 stores a first library in which structure parameters representing the surface structures of the wafer W which are expected to be formed after etching is performed with the resist pattern as a mask and then a polymer 8 is removed and before the resist layer 6 is removed and phase difference distributions and amplitude displacement distributions which have been calculated for the surface structures in advance are registered in an association manner.

Further, the library storage unit 321 stores a second library in which structure parameters representing the surface structures of the wafer W which are expected to be formed after etching is performed with the resist pattern as a mask and then the polymer 8 and the resist layer 6 are removed and phase difference distributions and amplitude displacement distributions which have been calculated for the surface structures in advance are registered in an association manner.

The analyzing unit 322 switches the library for use in response to the instruction from the system control apparatus

40. The analyzing unit 322 analyzes phases Wp reflected light and Ws reflected light and intensities Ip reflected light and Is reflected light at each wavelength λ of the reflected light based on the electrical signal supplied from the optical unit 31. Further, the analyzing unit 322 calculates the phase difference Δ and the amplitude displacement Ψ from phases Wp incident light and Ws incident light and intensities Ip incident light and Is incident light at each wavelength λ of the light applied to the wafer W and the analyzed phases Wp reflected light and Ws reflected light and intensities Ip reflected light and Is reflected light at each wavelength λ of the reflected light through use of Equation 1 and Equation 2, so as to find the phase difference distribution and the amplitude displacement distribution.

The analyzing unit 322 performs pattern matching of the found phase difference distribution and amplitude displacement distribution each of to the phase difference distributions and amplitude displacement distributions registered in the first and second libraries to retrieve from the first library a phase difference distribution and an amplitude displacement distribution which are approximate to the found phase difference distribution and amplitude displacement distribution, and to determine whether evaluation of the surface structure of the wafer W is possible or not.

The analyzing unit 322 retrieves from the first library the phase difference distribution and amplitude displacement distribution which are approximate to the found phase difference distribution and amplitude displacement distribution, and then estimates the surface structure of the wafer W from the structure parameter corresponding to the retrieved phase difference distribution and amplitude displacement distribution.

On the other hand, if the analyzing unit 322 cannot retrieve from the first library the phase difference distribution and amplitude displacement distribution which are approximate to the found phase difference distribution and amplitude displacement distribution because, for example, the resist layer 6 is significantly changed in shape and composition due to the etching processing, it determines that the evaluation of the surface structure of the wafer W is impossible (evaluation failure) and notifies the system control apparatus 40 of the fact.

After the etching processing and the in situ ashing processing are performed for the wafer W in the reduced-pressure processing apparatus 10, the system control apparatus 40 controls the carrier mechanism 60 to carry the wafer W out of the reduced-pressure processing apparatus 10 and carry the carried-out wafer W to the structure determination apparatus 30, and sets the library to be used by the structure determination apparatus 30 to the first library.

When notified from the analyzing unit 322 that the evaluation is impossible, the system control apparatus 40 suspends the subsequent processing for the wafer W. The system control apparatus 40 controls the carrier mechanism 60 to carry the wafer W out of the structure determination apparatus 30 and carry the carried-out wafer W to the solution treatment apparatus 20. After the resist layer 6 is removed in the solution treatment apparatus 20, the system control apparatus 40 carries the wafer W out of the solution treatment apparatus 20, carries the carried-out wafer W again to the structure determination apparatus 30, and sets the library to be used by the structure determination apparatus 30 to the second library.

Next, referring to a flowchart shown in FIG. 15 and cross-sectional views of the wafer W in steps shown in FIGS. 16A to 16D, the processing operation of the processing system 3 will be described taking as an example a case in which a plurality of contact holes 7 are formed in a wafer W and the surface structure of the wafer W formed with the contact holes 7 is determined.

First, the wafer W is carried to a not-shown oxidizing apparatus. The oxidizing apparatus performs an oxidation treatment to form a $SiO_2$ layer 5 within the surface region of the wafer W.

Then, the wafer W formed with the $SiO_2$ layer 5 within the surface region is carried to a not-shown resist coating apparatus. The resist coating apparatus applies a resist onto the $SiO_2$ layer 5. Subsequently, the wafer W coated with the resist is carried to a not-shown aligner. The aligner performs exposure processing for the resist applied on the surface of the wafer W. Subsequently, the wafer W subjected to the exposure processing is carried to a not-shown developing apparatus. The developing apparatus performs a developing treatment for the resist applied on the surface of the wafer W to form a resist pattern for forming the contact hole shown in FIG. 16A. Thereafter, the wafer W having the resist pattern formed on the surface is carried out of the developing apparatus.

The system control apparatus 40 controls the carrier mechanism 60 to carry the wafer W housed in the load port 50 to the alignment unit 70, which aligns the wafer W. Then, a gate valve 114 of a carry in/out port 113 is opened, and the system control apparatus 40 carries the wafer W, which has been carried out of the developing apparatus, into a chamber 11 of the reduced-pressure processing apparatus 10 and mounts the carried-in wafer W on a susceptor 12. Thereafter, the system control apparatus 40 retracts the carrier mechanism 60 from the inside of the chamber 11 and closes the gate valve 114. The reduced-pressure processing apparatus 10 drives a raising and lowering mechanism 123 to raise the susceptor 12 with the wafer W mounted thereon together with a susceptor supporting table 121 to a predetermined position. The reduced-pressure processing apparatus 10 evacuates the chamber 11 using an exhauster 112 to a predetermined reduced-pressure atmosphere, for example, a pressure of 0.01 Pa and lower. The reduced-pressure processing apparatus 10 applies direct current to an electrostatic chuck provided on the susceptor 12 to electrostatically attract the wafer W to the susceptor 12.

The reduced-pressure processing apparatus 10 opens a valve 135 of a gas introduction pipe 134 to diffuse the etching gas composed of $C_4F_8$, argon, and oxygen supplied from a gas supply source 137 in a diffusion part 132a, and then introduces it into the chamber 11 through gas holes 131a. The reduced-pressure processing apparatus 10 applies a high-frequency voltage of 0.1 MHz to 13 MHz to the susceptor 12 and a high-frequency voltage of 13 MHz to 150 MHz to an upper electrode 13 so as to generate a high density plasma gas between the susceptor 12 and the upper electrode 13. The reduced-pressure processing apparatus 10 selectively etches the surface of the wafer W using the generated plasma gas with the resist pattern as a mask (Step S301). This etching processing forms the contact hole 7 shown in FIG. 16B in the $SiO_2$ layer 5 on the wafer W and causes the polymer 8 to attach to the surfaces of the resist layer 6 and the contact hole 7.

After completion of the etching processing, the reduced-pressure processing apparatus 10 stops the application of the high-frequency voltages to the susceptor 12 and the upper electrode 13 and closes the valve 135 of the gas introduction pipe 134. Further, the reduced-pressure processing apparatus 10 brings the inside the chamber 11 into an in situ ashing atmosphere.

Figure 16A:
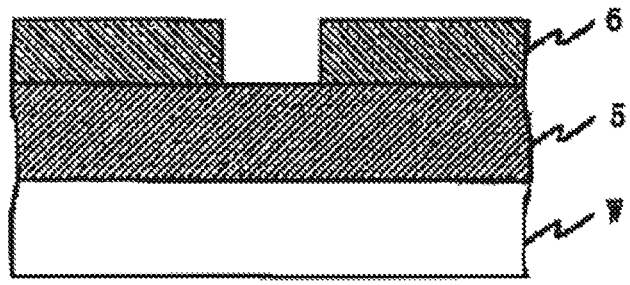
FIGS. 16A to 16D are cross-sectional views showing the structure of the wafer in steps of the processing operation according to the third embodiment of the present invention.
Figure 16B:
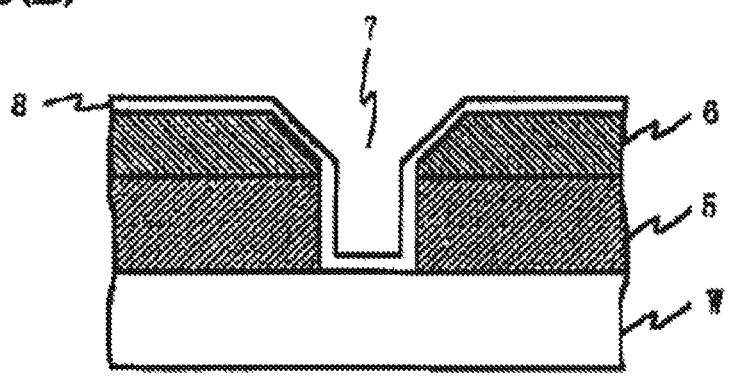
Figure 16C:
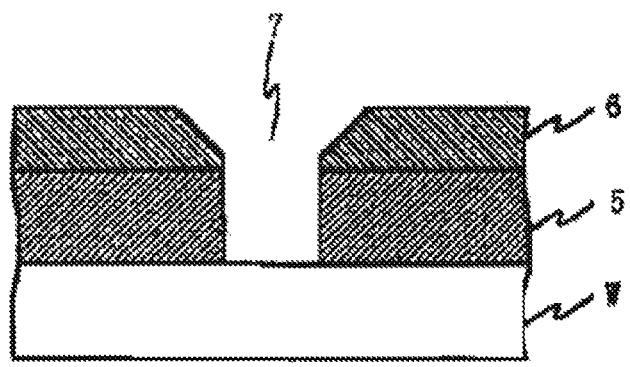

The reduced-pressure processing apparatus 10 opens the valve 135 of the gas introduction pipe 134 to diffuse the ashing gas composed of $O_2$ supplied from the gas supply source 137 in the diffusion part 132a, and then introduces it into the chamber 11 through the gas holes 131a. The reduced-pressure processing apparatus 10 applies high-frequency voltages to the susceptor 12 and the upper electrode 13 so as to generate a high density plasma gas between the susceptor 12 and the upper electrode 13. The reduced-pressure processing apparatus 10 performs the in situ ashing processing for the wafer W using the generated plasma gas to thereby remove, as shown in FIG. 16C, the resist layer 6 and the polymer 8 attached to the surface of the contact hole 7 (Step S302).

After completion of the in situ ashing processing, the reduced-pressure processing apparatus 10 stops the application of the high-frequency voltages to the susceptor 12 and the upper electrode 13 and closes the valve 135 of the gas introduction pipe 134. Further, the reduced-pressure processing apparatus 10 stops the application of the direct current to the susceptor 12 and returns the inside of the chamber 11 to a normal-pressure atmosphere. Further, the reduced-pressure processing apparatus 10 drives the raising and lowering mechanism 123 to lower the susceptor 12 with the wafer W mounted thereon together with the susceptor supporting table 121 to a predetermined position. The system control apparatus 40 opens the gate valve 114, carries the wafer W from which the polymer 8 has been removed out of the reduced-pressure processing apparatus 10, and closes the gate valve 114 after the carrying out. The system control apparatus 40 carries the wafer W, which has been carried out of the reduced-pressure processing apparatus 10, to the structure determination apparatus 30, mounts the carried wafer W on the mounting table 311 of the structure determination apparatus 30, and sets the library to be used by the structure determination apparatus 30 to the first library (Step S303).

The optical unit 31 emits white light from the light emitter 312 toward the wafer W, converts the white light into linearly polarized light by the polarizer 313, and applies the converted linearly polarized light to the wafer W (Step S304). The optical unit 31 receives at the light receiver 315 the polarized light reflected by the wafer W and transmitted through the analyzer 314, converts the received polarized light into an electrical signal, and supplies the converted electrical signal to the structure determination unit 32.

The structure determination unit 32 analyzes phases Wp reflected light and Ws reflected light and intensities Ip reflected light and Is reflected light at each wavelength λ of the reflected light based on the supplied electrical signal. Further, the structure determination unit 32 calculates the phase difference Δ and the amplitude displacement Ψ from phases Wp incident light and Ws incident light and intensities Ip incident light and Is incident light at each wavelength λ of the light applied to the wafer W and the analyzed phases Wp reflected light and Ws reflected light and intensities Ip reflected light and Is reflected light at each wavelength λ of the reflected light through use of Equation 1 and Equation 2, so as to find the phase difference distribution and the amplitude displacement distribution (Step S305).

The structure determination unit 32 performs pattern matching of the found phase difference distribution and amplitude displacement distribution to each of the phase difference distributions and amplitude displacement distributions registered in the first library to retrieve from the first library a phase difference distribution and an amplitude displacement distribution which are approximate to the calculated phase difference distribution and amplitude displacement distribution, and to determine whether evaluation of the surface structure of the wafer W is possible or not (Step S306).

If the structure determination unit 32 retrieves from the first library the phase difference distribution and amplitude displacement distribution which are approximate to the found phase difference distribution and amplitude displacement distribution (YES in Step S306), it estimates the surface structure of the wafer W from the structure parameter corresponding to the retrieved phase difference distribution and amplitude displacement distribution (Step S307).

On the other hand, if the structure determination unit 32 cannot retrieve from the first library the phase difference distribution and amplitude displacement distribution which are approximate to the found phase difference distribution and amplitude displacement distribution because, for example, the resist layer 6 is significantly changed in shape and composition due to the etching processing (NO in Step S306), it determines that the evaluation of the surface structure of the wafer W is impossible and notifies the system control apparatus 40 of the fact. When notified from the structure determination unit 32 that the evaluation is impossible, the system control apparatus 40 controls the carrier mechanism 60 to carry the wafer W out of the structure determination apparatus 30, carry the carried-out wafer W into the solution treatment apparatus 20, and mount the carried-in wafer W on a spin chuck 22.

Figure 16D:
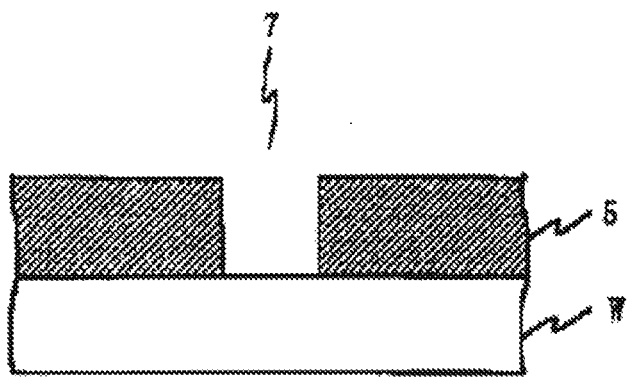

The solution treatment apparatus 20 sucks the mounted wafer W onto the spin chuck 22 with vacuum and rotates the wafer W sucked with vacuum by a motor 23. The solution treatment apparatus 20 discharges the resist layer removing solution composed of, for example, hydrofluoric acid (HF) or sulfuric acid ($H_2SO_4$), which is supplied from a first chemical supply unit 24, from a first chemical discharge nozzle 211 onto the surface of the wafer W which is being rotated by the motor 23. The solution treatment apparatus 20 utilizes the centrifugal force generated by the rotation to evenly spread the discharged resist layer removing solution over the surface of the wafer W, thereby removing the resist layer 6 on the surface of the wafer W as shown in FIG. 16D (Step S308).

The solution treatment apparatus 20 discharges the pure water or IPA solution, which is supplied from a second chemical supply unit 25, from a second chemical discharge nozzle 212 onto the surface of the wafer W which is being rotated by the motor 23. The solution treatment apparatus 20 utilizes the centrifugal force generated by the rotation to evenly spread the discharged pure water or IPA solution over the surface of the wafer W, thereby rinsing the surface of the wafer W from which the resist layer 6 has been removed. The solution treatment apparatus 20 allows the motor 23 to rotate the wafer W at a higher speed to dry by spin the rinsed wafer W. The system control apparatus 40 carries the wafer W from which the resist layer 6 has been removed to the structure determination apparatus 30, mounts the carried wafer W on the mounting table 311 of the structure determination apparatus 30, and sets the library to be used by the structure determination apparatus 30 to the second library (Step S309).

The optical unit 31 emits white light from the light emitter 312 toward the wafer W, converts the white light into linearly polarized light by the polarizer 313, and applies the converted linearly polarized light to the wafer W (Step S310). The optical unit 31 receives at the light receiver 315 the polarized light reflected by the wafer W and transmitted through the analyzer 314, converts the received polarized light into an electrical signal, and supplies the converted electrical signal to the structure determination unit 32.

The structure determination unit 32 analyzes phases Wp reflected light and Ws reflected light and intensities Ip reflected light and Is reflected light at each wavelength λ of the reflected light based on the supplied electrical signal. Further, the structure determination unit 32 calculates the phase difference Δ and the amplitude displacement Ψ from phases Wp incident light and Ws incident light and intensities Ip incident light and Is incident light at each wavelength λ of the light applied to the wafer W and the analyzed phases Wp reflected light and Ws reflected light and intensities Ip reflected light and Is reflected light at each wavelength λ of the reflected light through use of Equation 1 and Equation 2, so as to find the phase difference distribution and the amplitude displacement distribution (Step S311).

The structure determination unit 32 performs pattern matching of the found phase difference distribution and amplitude displacement distribution to each of the phase difference distributions and amplitude displacement distributions registered in the second library to retrieve from the second library a phase difference distribution and an amplitude displacement distribution which are approximate to the calculated phase difference distribution and amplitude displacement distribution (Step S312).

Further, the structure determination unit 32 estimates the surface structure of the wafer W from the structure parameter corresponding to the retrieved phase difference distribution and amplitude displacement distribution (Step S307).

According to the above-described processing operation, the polymer 8 having unclear shape and composition is removed, so that the processing system 3 can specify the optical constant n value (refractive index) and the k value (absorption coefficient) on the surface of the wafer W to accurately nondestructively determine by Ellipsometry the surface structure of the wafer W.

Moreover, the processing system 3 does not remove the resist layer 6 every time to determine the surface structure of the wafer W, but does remove the resist layer 6, to determine the surface structure of the wafer W, only when the processing system 3 cannot specify the surface structure of the wafer W with the resist layer 6 kept applied thereon such as when the resist layer 6 applied on the wafer W is significantly changed in shape and composition, so that the throughput of the entire processing can be improved.

Fourth Embodiment

A processing system 4 according to a fourth embodiment of the present invention will be described below with reference to the drawings. Note that the description of the same configuration as that of the processing systems 1, 2, and 3 according to the above-described first, second, and third embodiments will be omitted.

Figure 17:
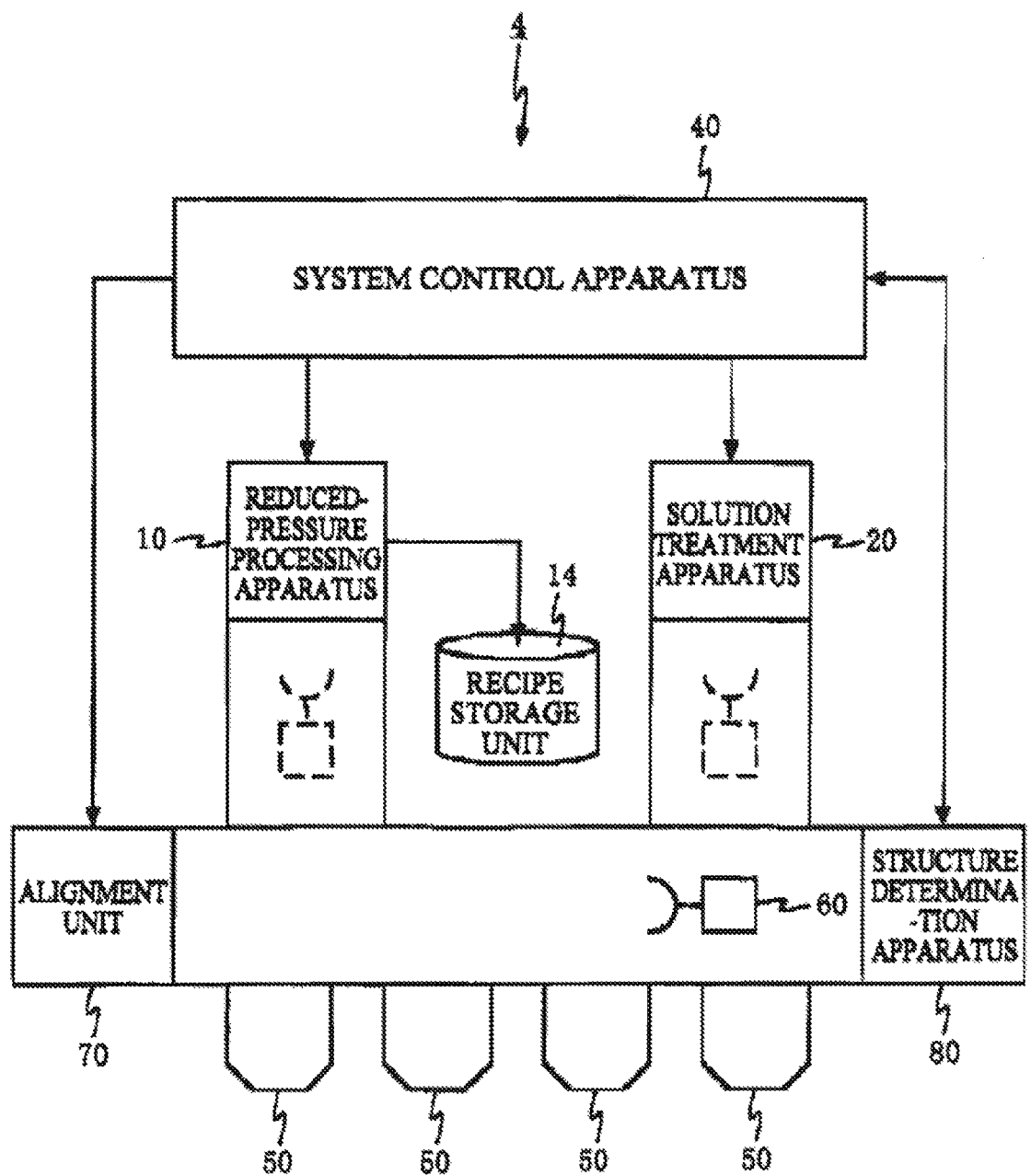
FIG. 17 is a diagram showing the configuration of a processing system according to the fourth embodiment of the present invention.

The processing system 4, as shown in FIG. 17, is composed of a reduced-pressure processing apparatus 10, a recipe storage unit 14, a solution treatment apparatus 20, a structure determination apparatus 80, a system control apparatus 40, load ports 50, a carrier mechanism 60, and an alignment unit 70, performs an etching processing for a wafer that is a workpiece, and determine by Reflectometry the surface structure of the wafer W after the etching processing.

The reduced-pressure processing apparatus 10 selectively performs an etching processing for the wafer W with a resist pattern as a mask under a reduced-pressure atmosphere. Note that the reduced-pressure processing apparatus 10 uses a mixed gas composed of $C_4F_8$, argon, and oxygen as the etching gas.

The solution treatment apparatus 20 removes an unnecessary portion such as a polymer 8 or the like attached to the surface of the wafer W, rinses the wafer W from which the polymer 8 has been removed, and dries by spin the rinsed wafer W.

The structure determination apparatus 80 is composed of an optical unit 81 and a structure determination unit 82 and determines the surface structure of the wafer W by Reflectometry. The optical unit 81 is composed of a mounting table 811, a light emitter 812, a reflecting mirror 813, a lens 814, and a light receiver 815 and applies light to the wafer W and receives reflected light from the wafer W.

The structure determination unit 82 switches the multiple regression equation for use in response to the instruction from the system control apparatus 40. The structure determination unit 82 estimates the surface structure of the wafer W from the ratio of the intensity of the light applied to the wafer W to the intensity of the light reflected from the wafer W (reflectance). Further, the structure determination unit 82 stores in the ROM predetermined multiple regression equations capable of calculating the structure parameter by multiple regression analysis using the reflectance as a variable.

These multiple regression equations are a first multiple regression equation for calculating the structure parameter of the wafer W before wet processing (the wafer W having the polymer attached to the surface) and a second multiple regression equation for calculating the structure parameter of the wafer W after the etching processing and the wet processing (the wafer W from which the polymer has been removed).

The structure determination unit 82 analyzes an intensity I reflected light at each wavelength λ, of the reflected light based on the electrical signal supplied from the optical unit 81. Further, the structure determination unit 82 calculates the reflectance (=I reflected light/I incident light) from the an intensity I incident light at each wavelength λ of the light applied to the wafer W and the analyzed intensity I reflected light at each wavelength λ of the reflected light.

The structure determination unit 82 carries out multiple regression analysis using the calculated reflectance (=I reflected light/I incident light) and the first multiple regression equation stored in the ROM. If the structure determination unit 82 can calculate the structure parameter by the multiple regression analysis within a predetermined period, it estimates the surface structure of the wafer W from the calculated structure parameter. The structure determination unit 82 supplies the calculated structure parameter to the system control apparatus 40.

On the other hand, if the structure determination unit 82 cannot calculate the structure parameter by the multiple regression analysis within the predetermined period because of, for example, the polymer or the like attached to the surface of the wafer W due to the etching processing, it determines that the evaluation of the surface structure of the wafer W is impossible (evaluation failure) and notifies the system control apparatus 40 of the fact.

After the etching processing is performed for the wafer W in the reduced-pressure processing apparatus 10, the system control apparatus 40 controls the carrier mechanism 60 to carry the wafer W out of the reduced-pressure processing apparatus 10 and carry the carried-out wafer W to the structure determination apparatus 80, and sets the multiple regression equation to be used by the structure determination apparatus 80 to the first multiple regression equation.

When notified from the structure determination unit 82 that the evaluation is impossible, the system control apparatus 40 suspends the subsequent processing for the wafer W. The system control apparatus 40 controls the carrier mechanism 60 to carry the wafer W out of the structure determination apparatus 80 and carry the carried-out wafer W to the solution treatment apparatus 20. After a resist layer 6 is removed in the solution treatment apparatus 20, the system control apparatus 40 carries the wafer W out of the solution treatment apparatus 20, carries the carried-out wafer W again to the structure determination apparatus 80, and sets the multiple regression equation to be used by the structure determination apparatus 80 to the second multiple regression equation.

When the setting of the etching condition of the reduced-pressure processing apparatus 10 is changed based on the surface structure evaluated in the structure determination apparatus 80, the system control apparatus 40 restarts the processing for the wafer W.

Figure 18:
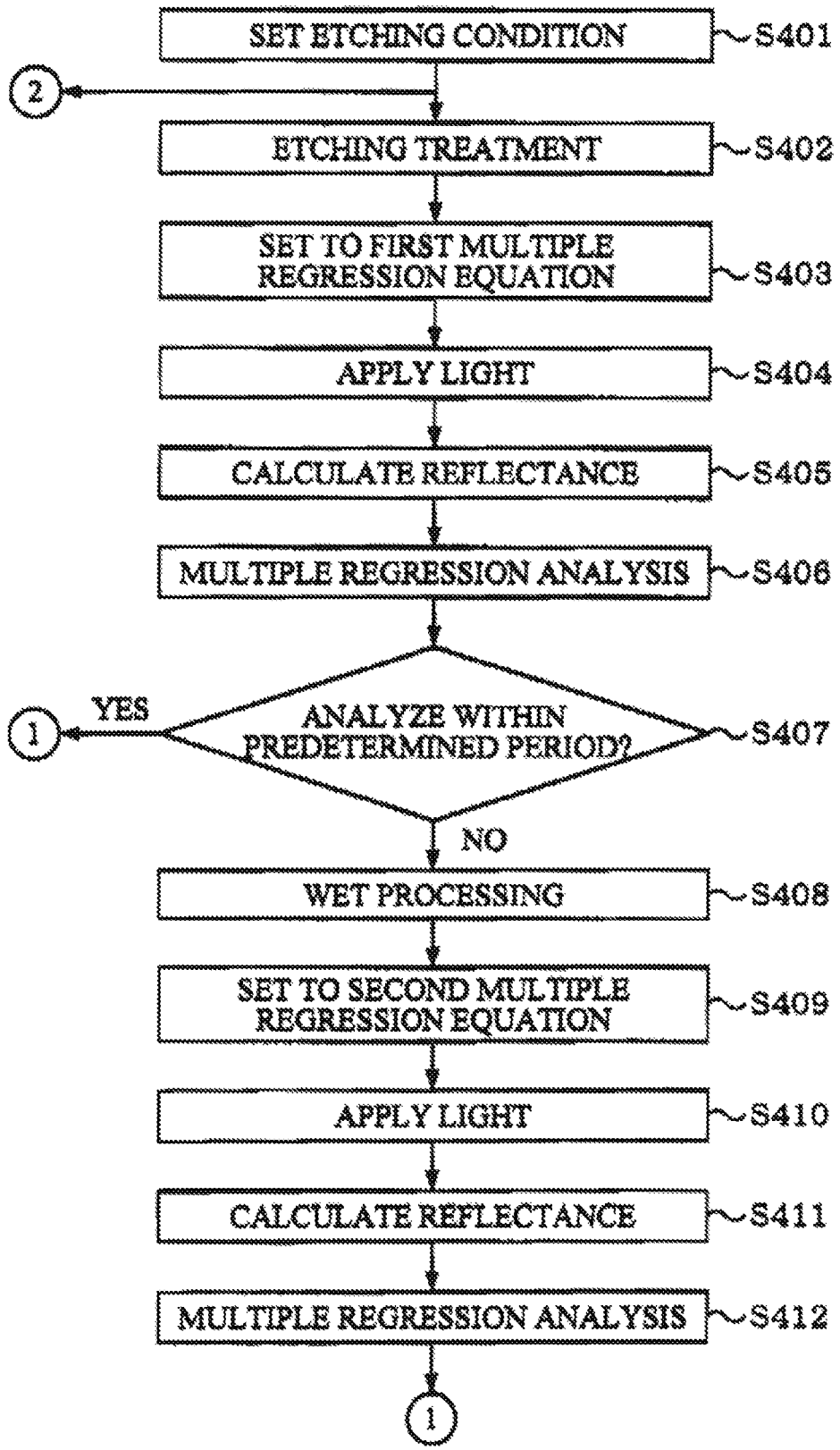
FIG. 18 is a flowchart showing a processing operation according to the fourth embodiment of the present invention.
Figure 19:
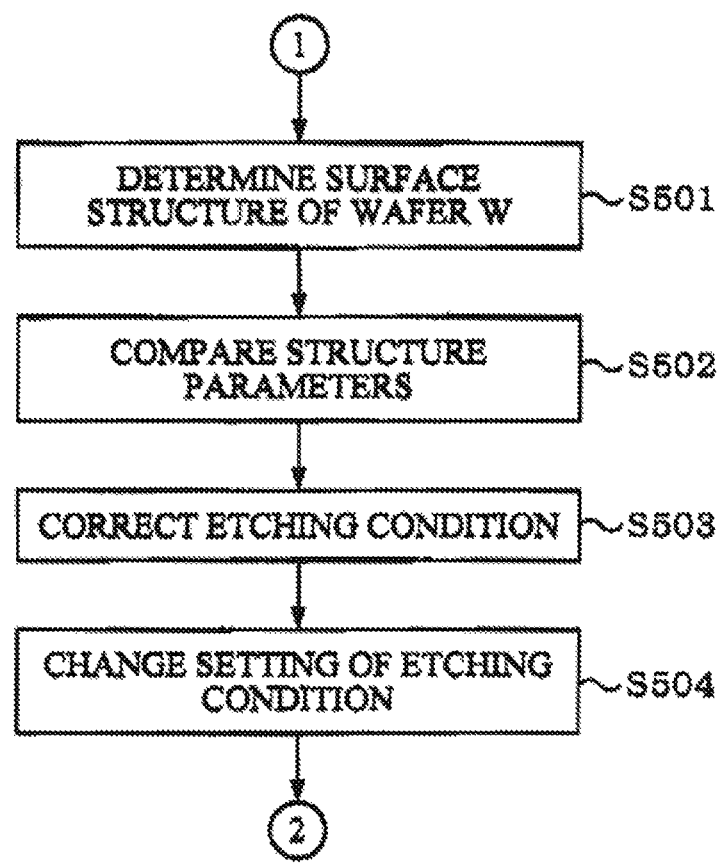
FIG. 19 is a flowchart showing a processing operation according to the fourth embodiment of the present invention.
Figure 20A:
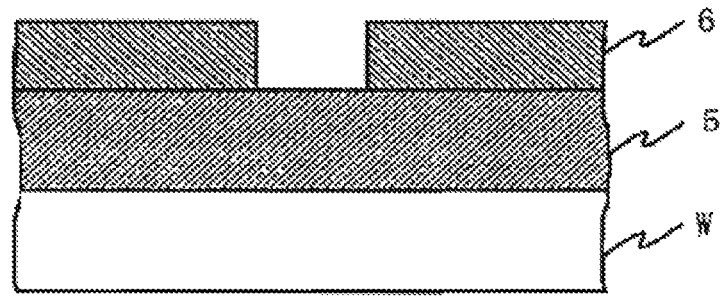
FIGS. 20A to 20C are cross-sectional views showing the structure of the wafer in steps of the processing operation according to the fourth embodiment of the present invention.
Figure 20B:
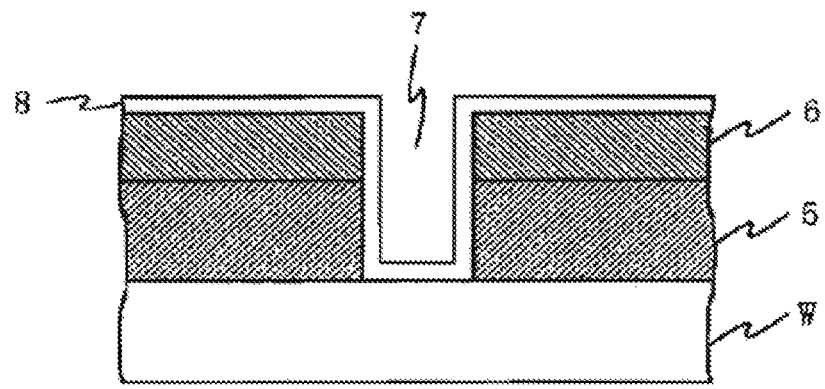
Figure 20C:
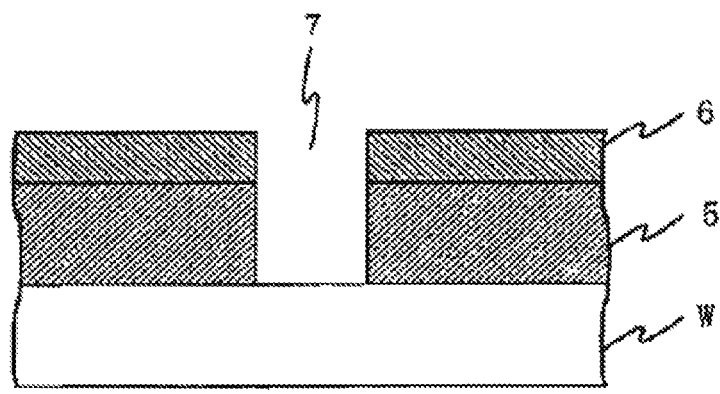

Next, referring to a flowchart shown in FIG. 18 and FIG. 19 and cross-sectional views of the wafer W in steps shown in FIGS. 20A to 20C, the processing operation of the processing system 4 will be described taking as an example a case in which a plurality of contact holes 7 are formed in a wafer W and the surface structure of the wafer W formed with the contact holes 7 is determined to feed back the etching condition.

First, the wafer W is carried to a not-shown oxidizing apparatus. The oxidizing apparatus performs an oxidation treatment to form a $SiO_2$ layer within the surface region of the wafer W.

Then, the wafer W formed with the $SiO_2$ layer 5 within the surface region is carried to a not-shown resist coating apparatus. The resist coating apparatus applies a resist onto the $SiO_2$ layer 5. Subsequently, the wafer W coated with the resist is carried to a not-shown aligner. The aligner performs exposure processing for the resist applied on the surface of the wafer W. Subsequently, the wafer W subjected to the exposure processing is carried to a not-shown developing apparatus. The developing apparatus performs a developing treatment for the resist applied on the surface of the wafer W to form a resist pattern for forming the contact hole shown in FIG. 20A. Thereafter, the wafer W having the resist pattern formed on the surface is carried out of the developing apparatus.

The system control apparatus 40 controls the carrier mechanism 60 to carry the wafer W housed in the load port 50 to the alignment unit 70, which aligns the wafer W. Then, a gate valve 114 of a carry in/out port 113 is opened, and the system control apparatus 40 carries the wafer W, which has been carried out of the developing apparatus, into a chamber 11 of the reduced-pressure processing apparatus 10 and mounts the carried-in wafer W on a susceptor 12. Thereafter, the system control apparatus 40 retracts the carrier mechanism 60 from the inside of the chamber 11 and closes the gate valve 114. The reduced-pressure processing apparatus 10 drives a raising and lowering mechanism 123 to raise the susceptor 12 with the wafer W mounted thereon together with a susceptor supporting table 121 to a predetermined position. The reduced-pressure processing apparatus 10 evacuates the chamber 11 using an exhauster 112 to a predetermined reduced-pressure atmosphere, for example, a pressure of 0.01 Pa and lower. The reduced-pressure processing apparatus 10 applies direct current to an electrostatic chuck provided on the susceptor 12 to electrostatically attract the wafer W to the susceptor 12.

The reduced-pressure processing apparatus 10 selects an optimal recipe from the recipe storage unit 14 based on the surface structure of the wafer W with the plurality of contact holes designated by an input unit and stores the etching condition (Gr) registered in the selected optimal recipe into the memory to thereby (initially) set the etching condition (Step S401).

The reduced-pressure processing apparatus 10 supplies the structure parameter representing the surface structure of the wafer W designated by the input unit and the set etching condition (Or) to the system control apparatus 40. The system control apparatus 40 stores the supplied structure parameter and (initially) set etching condition into the memory.

The reduced-pressure processing apparatus 10 opens, under the set etching condition (Or), a valve 135 of a gas introduction pipe 134 to diffuse the mixed gas composed of $C_4F_5$, argon, and oxygen supplied from a gas supply source 137 in a diffusion part 132a, and then introduces it into a chamber 11 through gas holes 131a. The reduced-pressure processing apparatus 10 applies high-frequency voltages to the susceptor 12 and an upper electrode 13 so as to generate a high density plasma gas between the susceptor 12 and the upper electrode 13. The reduced-pressure processing apparatus 10 selectively etches the surface of the wafer W using the generated plasma gas with the resist pattern as a mask (Step S402). This etching processing forms a contact hole 7 shown in FIG. 20B in the $SiO_2$ layer 5 on the wafer W and causes the polymer 8 to attach to the surfaces of the resist layer 6 and the contact hole 7.

After completion of the etching processing, the reduced-pressure processing apparatus 10 stops the application of the high-frequency voltages to the susceptor 12 and the upper electrode 13 and closes the valve 135 of the gas introduction pipe 134. Further, the reduced-pressure processing apparatus 10 stops the application of the direct current to the susceptor 12 and returns the inside of the chamber 11 to a normal-pressure atmosphere. Further, the reduced-pressure processing apparatus 10 drives the raising and lowering mechanism 123 to lower the susceptor 12 with the wafer W mounted thereon together with the susceptor supporting table 121 to a predetermined position. The system control apparatus 40 opens the gate valve 114, carries the wafer W with the polymer 8 attached thereto out of the reduced-pressure processing apparatus 10, and closes the gate valve 114 after the carrying out. The system control apparatus 40 carries the wafer W, which has been carried out of the reduced-pressure processing apparatus 10, into the structure determination apparatus 80, mounts the carried-in wafer W on the mounting table 811, and sets the multiple regression equation to be used by the structure determination apparatus 80 to the first multiple regression equation. (Step S403)

The optical unit 81 emits white light from the light emitter 812 horizontally with respect to the surface of the ground, reflects the white light vertically downward by the reflecting mirror 813 to apply the reflected white light to the wafer W via the lens 814 (Step S404). The optical unit 81 receives reflected light from the wafer W, converts the received reflected light into an electrical signal, and supplies the converted electrical signal to the structure determination unit 82.

The structure determination unit 82 analyzes an intensity I reflected light at each wavelength % of the reflected light based on the electrical signal supplied from the optical unit 81. Further, the structure determination unit 82 calculates the reflectance (=I reflected light/I incident light) from an intensity I incident light at each wavelength λ of the light applied to the wafer W and the analyzed intensity I reflected light at each wavelength λ of the reflected light (Step S405).

The structure determination unit 82 carries out multiple regression analysis using the calculated reflectance (=I reflected light/I incident light) and the first multiple regression equation set based on the instruction of the system control apparatus 40 (Step S406).

If the structure determination unit 82 can calculate the structure parameter by the multiple regression analysis within a predetermined period (YES in Step S407), it estimates the surface structure of the wafer W from the calculated structure parameter (Step S501). The structure determination unit 82 supplies the calculated structure parameter to the system control apparatus 40.

The system control apparatus 40 compares the structure parameters stored in the memory to the structure parameter supplied from the structure determination unit 82, thereby comparing the depth of the contact hole or the like designated in the reduced-pressure processing apparatus 10 to the depth or the like of the actually formed contact hole (Step S502).

When the depth of the actually formed contact hole 7 is shallower than the depth of the designated contact hole, the system control apparatus 40 corrects the (initially) set etching condition Gr to Gr+ΔG so as to increase the gas flow rate to be supplied to the chamber 11 (Step S503). The system control apparatus 40 supplies the corrected etching condition (Gr+ΔG) to the reduced-pressure processing apparatus 10, thereby feeding back the etching condition to the reduced-pressure processing apparatus 10.

When the etching condition (Gr+ΔG) is supplied from the system control apparatus 40, the reduced-pressure processing apparatus 10 rewrites the etching condition stored in the memory from (Gr) to (Gr+ΔG) to thereby change the setting of the etching condition (Step S504).

On the other hand, if the structure determination unit 82 cannot calculate the structure parameter by the multiple regression analysis within the predetermined period because, for example, the resist layer is significantly changed in shape and composition due to the etching processing (NO in Step S407), it determines that the evaluation of the surface structure of the wafer W is impossible and notifies the system control apparatus 40 of the fact. When notified from the structure determination unit 82 that the evaluation is impossible, the system control apparatus 40 suspends the subsequent processing for the wafer W. Further, the system control apparatus 40 controls the carrier mechanism 60 to carry the wafer W out of the structure determination apparatus 80, carry the carried-out wafer W into the solution treatment apparatus 20, and mount the carried-in wafer W on a spin chuck 22.

The solution treatment apparatus 20 sucks the mounted wafer W on the spin chuck 22 with vacuum and rotates the wafer W sucked with vacuum by a motor 23. The solution treatment apparatus 20 discharges the polymer removing solution composed of, for example, hydrofluoric acid (HF) or sulfuric acid ($H_2SO_4$), which is supplied from a first chemical supply unit 24, from a first chemical discharge nozzle 211 to the surface of the wafer W which is being rotated by the motor 23. The solution treatment apparatus 20 utilizes the centrifugal force generated by the rotation to evenly spread the discharged polymer removing solution over the surface of the wafer W, thereby removing the polymer 8 attached to the surface of the wafer W as shown in FIG. 20C (Step S408).

The solution treatment apparatus 20 discharges the pure water or IPA solution, which is supplied from a second chemical supply unit 25, from a second chemical discharge nozzle 212 onto the surface of the wafer W which is being rotated by the motor 23. The solution treatment apparatus 20 utilizes the centrifugal force generated by the rotation to evenly spread the discharged pure water or IPA solution over the surface of the wafer W, thereby rinsing the surface of the wafer W from which the polymer 8 has been removed. The solution treatment apparatus 20 allows the motor 23 to rotate the wafer W at a higher speed to dry by spin the rinsed wafer W. The system control apparatus 40 carries the wafer W from which the resist layer 6 has been removed to the structure determination apparatus 80, mounts the carried wafer W on the mounting table 81 of the structure determination apparatus 80, and sets the multiple regression equation to be used by the structure determination apparatus 80 to the second multiple regression equation (Step S409).

The optical unit 81 emits white light from the light emitter 812 horizontally with respect to the surface of the ground, reflects the white light vertically downward by the reflecting mirror 813 to apply the reflected white light to the wafer W via the lens 814 (Step S410). The optical unit 81 receives reflected light from the wafer W, converts the received reflected light into an electrical signal, and supplies the converted electrical signal to the structure determination unit 82.

The structure determination unit 82 analyzes an intensity I reflected light at each wavelength λ of the reflected light based on the electrical signal supplied from the optical unit 81. Further, the structure determination unit 82 calculates the reflectance (=I reflected light/I incident light) from an intensity I incident light at each wavelength λ of the light applied to the wafer W and the analyzed intensity I reflected light at each wavelength λ of the reflected light (Step S411).

The structure determination unit 82 carries out multiple regression analysis using the calculated reflectance (=I reflected light/I incident light) and the second multiple regression equation set based on the instruction of the system control apparatus 40 to calculate the structure parameter (Step S412).

The structure determination unit 82 estimates the surface structure of the wafer W formed with the plurality of contact holes 7 from the calculated structure parameter (Step S501). The structure determination unit 82 supplies the calculated structure parameter to the system control apparatus 40.

The system control apparatus 40 compares the structure parameters stored in the memory to the structure parameter supplied from the structure determination unit 82, thereby comparing the depth of the contact hole or the like designated in the reduced-pressure processing apparatus 10 to the depth or the like of the actually formed contact hole (Step S502).

When the depth of the actually formed contact hole 7 is shallower than the depth of the designated contact hole, the system control apparatus 40 corrects the (initially) set etching condition Gr to Gr+ΔG' so as to increase the gas flow rate to be supplied to the chamber 11 (Step S503). The system control apparatus 40 supplies the corrected etching condition (Gr+ΔG') to the reduced-pressure processing apparatus 10, thereby feeding back the etching condition to the reduced-pressure processing apparatus 10.

When the etching condition (Gr+ΔG') is supplied from the system control apparatus 40, the reduced-pressure processing apparatus 10 rewrites the etching condition stored in the memory from (Gr) to (Gr+ΔG') to thereby change the setting of the etching condition (Step S504). When the setting of the etching condition is changed, the system control apparatus 40 restarts the subsequent processing for the wafer W.

According to the above-described processing operation, the polymer 8 having an unclear shape and composition is removed, so that the processing system 4 can specify the optical constant n value (refractive index) and the k value (absorption coefficient) on the surface of the wafer W to accurately nondestructively determine by Reflectometry the surface structure of the wafer W.

Further, the processing system 4 corrects the etching condition to be supplied to the reduced-pressure processing apparatus 10 from the surface structure of the wafer W which has been accurately determined by Reflectometry and feeds back the etching condition, whereby the processing system 4 can perform an accurate and uniform etching processing for the wafer W.

Moreover, the processing system 4 does not remove the polymer 8 every time to determine the surface structure of the wafer W, but does remove the polymer 8, to determine the surface structure of the wafer W, only when the processing system 4 cannot specify the surface structure of the wafer W with the polymer 8 kept attached thereto, so that the throughput of the entire processing can be improved.

Further, when the processing system 4 cannot specify the surface structure of the wafer W with the polymer 8 attached thereto, the processing system 4 suspends the subsequent processing for the wafer W, whereby it can manufacture the wafers W with high yields.

It should be noted that the present invention is not limited to the above-described embodiments, but various modifications and applications are possible. Modified aspects of the above-described embodiments applicable to the present invention will be described below.

In the above-described first, second, third, and fourth embodiments, the processing systems 1, 2, 3 and 4 evaluate the surface structure (shape) of the wafer W after the etching processing. The present invention, however, is not limited to this, and the processing systems 1, 2, 3 and 4 may evaluate the surface structure (ion concentration) of the wafer W after ion implantation.

Besides, in the above-described first, second, third, and fourth embodiments, the structure determination apparatuses 30 and 80 determine the surface structure of the wafer W formed with the plurality of contact holes. The present invention, however, is not limited to this, and the structure determination apparatuses 30 and 80 may determine the surface structure of a wafer W with STI (Shallow Trench Isolation) or a wafer W with the gate etched.

Further, in above-described the first, second, third, and fourth embodiments, the xenon lamp is used as the light emitters 312 and 812. The present invention, however, is not limited to this, and any lamp may be used as long as it emits white light, such as a heavy hydrogen lamp or the like.

Scatterometry in the above-described first and third embodiments is Ellipsometry, while Scatterometry in the second and fourth embodiments is Reflectometry. The present invention, however, is not limited to this, and any Scatterometry may be employed as long as it can determine the surface structure of the wafer W from the phase, intensity, and so on of reflected light obtained by applying light to the wafer W.

Furthermore, in the above-described first and third embodiments, the analyzing unit 322 corrects the phase difference distribution and the amplitude displacement distribution retrieved from the library by performing pattern matching to the found phase difference distribution and amplitude displacement distribution, and estimates the surface structure of the wafer W from the corrected structure parameter. The present invention, however, is not limited to this, and the analyzing unit 322 may perform pattern matching of the found phase difference distribution and amplitude displacement distribution to the phase difference distributions and amplitude displacement distributions registered in the library to retrieve from the library a phase difference distribution and an amplitude displacement distribution which are approximate to the found phase difference distribution and amplitude displacement distribution, and when the structure parameter corresponding to the retrieved phase difference distribution and amplitude displacement distribution falls within a predetermined range of convergence (GOF), the analyzing unit 322 may estimate the structure parameter of the wafer W from the above structure parameter. Further, the analyzing unit 322 may calculate the structure parameter by carrying out multiple regression analysis of the calculated phase difference $\Delta$ and amplitude displacement $\Psi$ and estimate the surface structure of the wafer W from the calculated structure parameter.

Besides, in the above-described second and fourth embodiments, the structure determination unit 82 calculates the structure parameter by carrying out the multiple regression analysis of the calculated reflectance and estimates the surface structure of the wafer W from the calculated structure parameter. The present invention, however, is not limited to this, and the determination unit 82 may perform pattern matching of the found phase difference distribution and amplitude displacement distribution to the phase difference distributions and amplitude displacement distributions registered in the library to retrieve from the library a phase difference distribution and an amplitude displacement distribution which are approximate to the found phase difference distribution and amplitude displacement distribution, and if the structure parameter corresponding to the retrieved phase difference distribution and amplitude displacement distribution falls within a predetermined range of convergence (GOF), the determination unit 82 may estimate the structure parameter of the wafer W from the above structure parameter. Further, the determination unit 82 may find a reflectance distribution from the calculated reflectance, correct a reflectance distribution retrieved from the library by performing pattern matching to the reflectance distribution, and estimate the surface structure of the wafer W from the corrected structure parameter.

Furthermore, in the above-described second and fourth embodiments, the parameter of the etching condition is the flow rate of the etching gas. The present invention, however, is not limited to this, and the pressure in the chamber 11, the power and the frequency of the first and second high-frequency power sources, the kind of gas, the temperature of the susceptor 12, the gap between the susceptor 12 and the upper electrode 13, or the like may be used as the parameter of etching condition.

Besides, in the above-described first embodiment, the processing system 1 only determines the surface structure of the wafer W. The present invention, however, is not limited to this, and the processing system 1 may correct the etching condition such as the pressure in the chamber 11, the flow rate of the etching gas, or the like, and feed back the corrected etching condition to the reduced-pressure processing apparatus 10.

Moreover, in the above-described first embodiment, the solution treatment apparatus 20 removes the polymer 8 and the resist layer 6 on the surface of the wafer W. The present invention, however, is not limited to this, and the solution treatment apparatus 20 may remove only the polymer 8 attached to the surface of the wafer W.

Further, in the above-described second embodiment, the reduced-pressure processing apparatus 10 only removes the deteriorated hard layer 9 formed within the surface region of the resist layer 6 and the damaged layer A formed within the bottom region of the contact hole 7. The present invention, however, is not limited to this, and the reduced-pressure processing apparatus 10 may remove the resist layer 6 as well as the deteriorated hard layer 9 and the damaged layer A.

Further, in the above-described second embodiment, the reduced-pressure processing apparatus 10 removes by ashing processing the deteriorated hard layer 9 formed in the resist layer 6 and the damaged layer A formed within the bottom region of the contact hole 7. The present invention, however, is not limited to this, and the deteriorated hard layer 9 and the damaged layer A may be removed by performing a light etching processing for them using a mixed gas composed of $CF_4$ and $O_2$.

Further, in the above-described second, third, and fourth embodiments, the same reduced-pressure processing apparatus 10 is used to perform the etching processing and the ashing processing for the wafer W. The present invention, however, is not limited to this, and it is also adoptable to perform the etching processing in the reduced-pressure processing apparatus 10 and to perform the ashing processing for the wafer W in a reduced-pressure processing apparatus different from the reduced-pressure processing apparatus 10.

Fifth Embodiment

A processing system 5 according to a fifth embodiment of the present invention will be described below with reference to the drawings.

Figure 21:
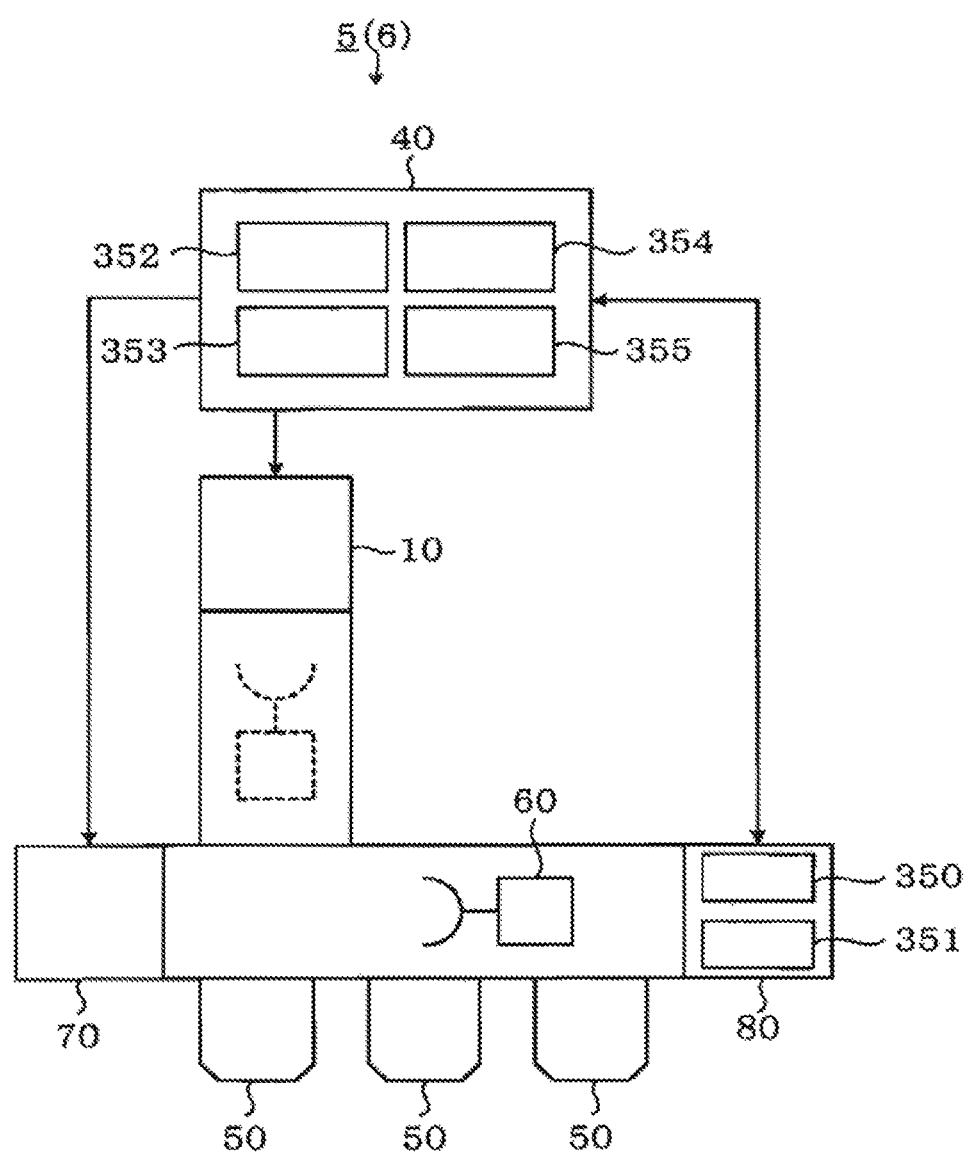
FIG. 21 is a diagram showing the configuration of a processing system according to a fifth and a sixth embodiment of the present invention.

The processing system 5 having a configuration similar to, for example, that of the above-described processing system 2 includes, as shown in FIG. 21, a reduced-pressure processing apparatus 10, a structure determination apparatus 80 as a surface structure measurement apparatus (a structure measurement apparatus), a system control apparatus 40 as a controller, load ports 50, a carrier mechanism 60, and an alignment unit 70. The processing system 5 can perform an etching processing for a wafer W that is a workpiece and measure by Reflectometry the dimension of the pattern structure formed in the surface of the wafer W (the surface structure of the wafer W) after the etching processing.

The reduced-pressure processing apparatus 10 can selectively perform an etching processing for the wafer W with a resist pattern as a mask under a reduced-pressure atmosphere. Note that the reduced-pressure processing apparatus 10 uses a mixed gas composed of $C_4F_8$, argon, and oxygen as the etching gas.

The structure determination apparatus 80 includes a measurement unit 350 and a computation unit 351 and can measure the dimension of the pattern structure formed in the surface of the wafer W, for example, by Reflectometry. The measurement unit 350 having a configuration similar to, for example, that of the above-described optical unit 81 includes, for example, a mounting table 811, a light emitter 812, a reflecting mirror 813, a lens 814, a light receiver 815, and so on to be able to apply light to the wafer W and receive reflected light from the wafer W.

The computation unit 351 has, for example, a CPU, an HD, a memory, and so on to be able to calculate the dimensions of the pattern structure in the wafer surface, such as the depth and line width of the actual groove in the wafer surface, for example, based on the information of the reflected light from the measurement unit 350.

The system control apparatus 40 includes, for example, a recipe storage unit 352, an apparatus parameter control unit 353, a computation unit 354, and a memory unit 355. The memory unit 355 stores, for example, permissible values of the dimensions of the pattern structure in the wafer surface after the etching processing for each recipe of wafer processing. The memory unit 355 of the system control apparatus 40 stores, for example, permissible values of a predetermined dimension in the depth direction and a predetermined dimension in the horizontal direction of the pattern structure in the wafer surface after the etching processing.

The recipe storage unit 352 stores a plurality of recipes of the apparatus parameters necessary for the etching processing, such as the gas flow rate of the processing gas, the power value of a high-frequency power source, and so on.

The apparatus parameter control unit 353 can transmit the apparatus parameters stored in the recipe storage unit 352 to the flow rate controller 136, high-frequency power sources 124 and 139, and so on to change the setting of the parameters of each apparatus.

The computation unit 354 of the system control apparatus 40 can compare the dimensions of the pattern structure in the wafer surface calculated by the structure determination apparatus 80 to the permissible values stored in the memory unit 355 to decide continuation or suspension of the etching processing in the reduced-pressure processing apparatus 10 based on the comparison result. The system control apparatus 40 can display a continuation message for the continuation and an error message for the suspension, for example, on a not-shown display unit provided in the processing system 5.

It should be note that the description of a configuration similar to that of the processing system 2 according to the above-described second embodiment will be omitted.

Figure 22:
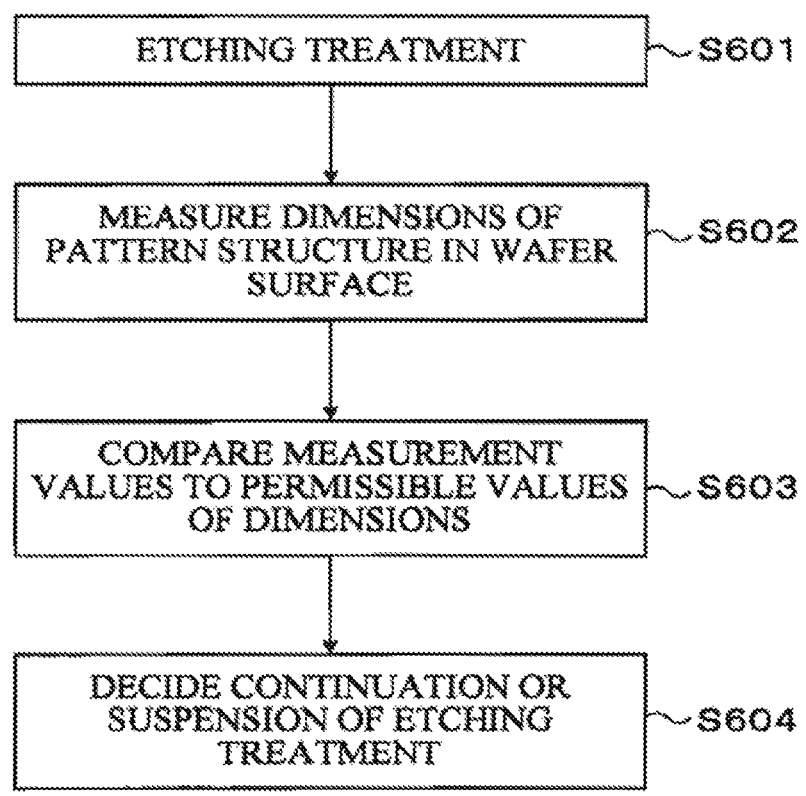
FIG. 22 is a flowchart of processing according to the fifth embodiment of the present invention.
Figure 23A:
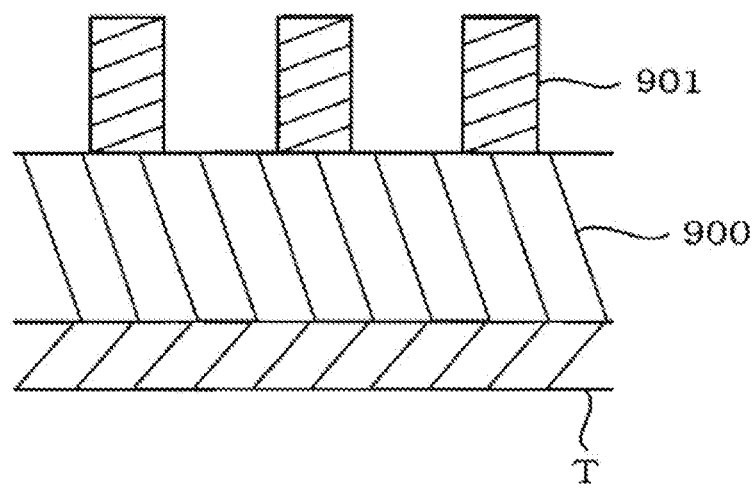
FIGS. 23A and 23B are vertical cross-sectional views showing the pattern structure in the surface of a test wafer before and after an etching processing.
Figure 23B:
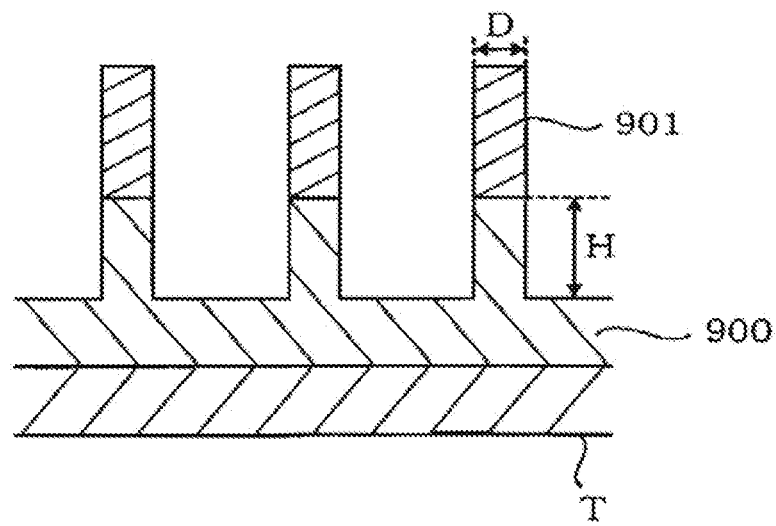

Next, processing performed in the processing system 5 will be described. FIG. 22 is a flowchart of the processing. First, as shown in FIG. 23A, a test wafer T having a simple structure in which only a film to be etched 900 and a resist film 901 patterned in the shape of lines are formed on a wafer surface is housed into the load port 50. Subsequently, the test wafer T is carried by the carrier mechanism 60 to the alignment unit 70 and aligned there, and thereafter carried to the reduced-pressure processing apparatus 10. The test wafer T which has been carried into the reduced-pressure processing apparatus 10 is subjected to an etching processing under a predetermined etching processing condition as in the above-described embodiments (S601 in FIG. 22). This etching processing eliminates the etching film to be etched 900 and resist film 901 as shown in FIG. 23B.

The test wafer T for which the etching processing has been completed in the reduced-pressure processing apparatus 10 is carried by the carrier mechanism 60 to the structure determination apparatus 80 where the dimensions of the pattern structure in the test wafer T after the etching processing, for example, the dimensions in two dimensional directions such as a depth dimension H in the depth direction of the film to be etched 900 and a line width D of the film to be etched 900 and the resist film 901 are measured by the measurement unit 350 and computation unit 351 (S602 in FIG. 22).

A permissible value $H_M$ of the depth dimension H of the film to be etched 900 and a permissible value $D_M$ of the line width D of the film to be etched 900 are set in the memory unit 355 of the system control apparatus 40.

When the measurement results of the depth dimension H and the line width D are outputted from the structure determination apparatus 80 to the system control apparatus 40, the computation unit 354 of the system control apparatus 40 compares the outputted depth dimension H and line width D to the respective permissible values $H_M$ and $D_M$ (S603 in FIG. 22). If, for example, either the depth dimension H or the line width D exceeds its permissible value, the computation unit 354 of the system control apparatus 40 decides suspension of the etching processing in the reduced-pressure processing apparatus 10, and the error message is displayed. On the other hand, if neither the depth dimension H nor the line width D exceeds its permissible value, the computation unit 354 of the system control apparatus 40 decides continuation of the etching processing in the reduced-pressure processing apparatus 10, and its continuation message is displayed (S604 in FIG. 22).

The test wafer T of which dimensions of the pattern structure in the wafer surface have been measured in the structure determination apparatus 80 is collected by the carrier mechanism 60 into the load port 50.

According to the fifth embodiment, it is possible to measure the dimension in the depth direction and the dimension in the horizontal direction of the pattern structure in the wafer surface at the same time by Reflectometry. Therefore, the measurement of the dimensions of the pattern structure can be performed more rapidly than in the prior art in which the dimensions in the two directions are measured in sequence. Further, it is possible to measure the dimensions of the pattern structure in the wafer surface without breaking the wafer W.

Incidentally, in the case in which the pattern structure in the wafer surface is grasped by image of the wafer W seen from a plane using a scanning electron microscope as in the prior art, when the line width of the film to be etched at the top portion is wider than the other portion such as when the line width of the film to be etched becomes wider as it goes downward, the wider portion is grasped as the line width, and therefore it is impossible to measure the line width at a desired position of the film to be etched. According to the present invention, which uses Reflectometry, it is possible to measure the line width at a desired position of the film to be etched at all times irrespective of a change in shape of the film to be etched. Accordingly, the dimensions of the pattern structure in the wafer surface can be accurately measured.

In addition, since the dimensions of the pattern structure in the wafer surface accurately measured as described above can be compared to the previously set permissible values so that the continuation or suspension of the etching processing can be decided based on the comparison result, it is possible to automatically determine whether the etching processing in the reduced-pressure processing apparatus 10 is proper or not to thereby automatically manage the reduced-pressure processing apparatus 10. This prevents human error which occurs when a person manages it.

Further, according to the embodiment, since the test wafer T having a pattern structure simpler than an ordinary product wafer is used for the measurement of the dimensions of the pattern structure in the wafer surface after the etching processing, the dimensions of the pattern structure in the wafer surface can be measured using a less expensive wafer.

In the fifth embodiment, the dimensions of the pattern structure in the wafer surface are measured by Reflectometry, but the dimensions of the surface structure may be measured by another Scatterometry, for example, Ellipsometry. Besides, in the above-described embodiment, the pattern in the form of lines is formed in the surface of the test wafer T, but it is also adoptable to form another pattern structure such as a contact hole and measure the dimensions of the pattern structure. While the dimensions in the two dimensional directions such as the depth direction and the horizontal direction in the surface of the test wafer T are measured in the above-described embodiment, the dimensions in three dimensional directions may be measured. For example, when contact holes are formed in the surface of the test wafer T, the depth and the lengths of lengthwise and crosswise diameters of the contact hole may be measured.

The dimensions of the pattern structure in the test wafer T are measured only to decide the continuation or suspension of the etching processing in the above-described fifth embodiment, but if the dimension of the pattern structure in the test wafer T is off its permissible value, the etching condition such as the pressure in the chamber 11, the etching time, the flow rate of the etching gas, or the like may be corrected based on the measurement value of the dimension so that the corrected etching condition may be fed forward to the reduced-pressure processing apparatus 10.

Sixth Embodiment

A processing system 6 according to a sixth embodiment of the present invention will be described below with reference to the drawings.

The processing system 6 having a configuration similar to, for example, that of the above-described processing system 5 shown in FIG. 21 includes a reduced-pressure processing apparatus 10 as an etching processing apparatus, a structure determination apparatus 80 as a surface structure measurement apparatus (a structure measurement apparatus), a system control apparatus 40 as a controller, load ports 50, a carrier mechanism 60, and an alignment unit 70. The processing system 6 can measure the dimension of the pattern structure in the surface (the surface structure) of a wafer W that is a workpiece before the etching processing, for example, by Reflectometry.

The reduced-pressure processing apparatus 10 can selectively perform an etching processing for the wafer W with a resist pattern as a mask, for example, for a predetermined set time under a reduced-pressure atmosphere. Into a chamber 11 of the reduced-pressure processing apparatus 10, oxygen gas as the etching gas can be supplied at a predetermined flow rate, for example, through a flow rate controller 136 and so on.

The structure determination apparatus 80 includes a measurement unit 350 and a computation unit 351 and can measure the dimension of the pattern structure in the surface of the wafer W, for example, by Reflectometry. The measurement unit 350 having a configuration similar to, for example, that of the above-described optical unit 81 includes, for example, a mounting table 811, a light emitter 812, a reflecting mirror 813, a lens 814, and a light receiver 815 to be able to apply light to the wafer W and receive reflected light from the wafer W.

The recipe storage unit 352 stores a plurality of recipes of the apparatus parameters (processing conditions) necessary for the etching processing, such as the gas flow rate of the processing gas, the power value of a high-frequency power source, and so on.

The apparatus parameter control unit 353 can transmit the apparatus parameters stored in the recipe storage unit 352 to the flow rate controller 136, high-frequency power sources 124 and 139, and so on to change the setting of the parameters of each apparatus.

The computation unit 351 has, for example, a CPU, an HD, a memory, and so on to be able to calculate the dimensions of the pattern structure in the surface of the wafer W, such as the depth and line width of the actual groove in the wafer surface, for example, based on the information of the reflected light from the measurement unit 350.

The system control apparatus 40 includes, for example, the recipe storage unit 352, the apparatus parameter control unit 353, a computation unit 354, and a memory unit 355. The memory unit 355 of the system control apparatus 40 stores, for example, data on correlation between the plurality of etching conditions and the elimination amounts of the pattern structure in the surface of the wafer W by the etching processing. The memory unit 355 of the system control apparatus 40 stores, for example, data on correlation between the etching processing time and the elimination amount in the depth direction by the etching processing as shown in FIG. 24A and data on correlation among the etching processing time, the supply flow rate of the etching gas, and the elimination amount of the line width by the etching processing as shown in FIG. 24B.

The computation unit 354 of the system control apparatus 40 can decide the etching processing condition so that the depth dimension and the line width after the etching processing are desired dimensions, for example, based on the depth dimension and the line width of the pattern structure in the surface of the wafer W which have been measured before the etching processing in the structure determination apparatus 80 and on the aforementioned correlation data stored in the memory unit 355. The computation unit 354 of the system control apparatus 40 can change, for example, the setting of the etching processing condition such as the initial etching processing time, supply flow rate of the etching gas, and so on which have been previously set in the recipe storage unit 352 to the aforementioned decided processing condition.

It should be note that the description of a configuration similar to that of the processing system 2 according to the above-described second embodiment will be omitted.

Figure 25:
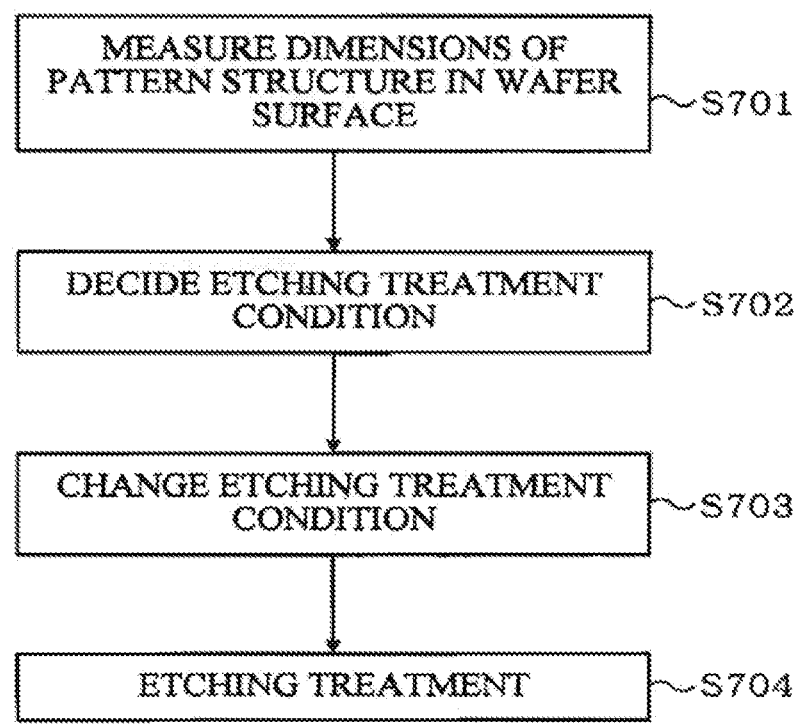
FIG. 25 is a flowchart showing processing according to the sixth embodiment of the present invention.
Figure 26A:
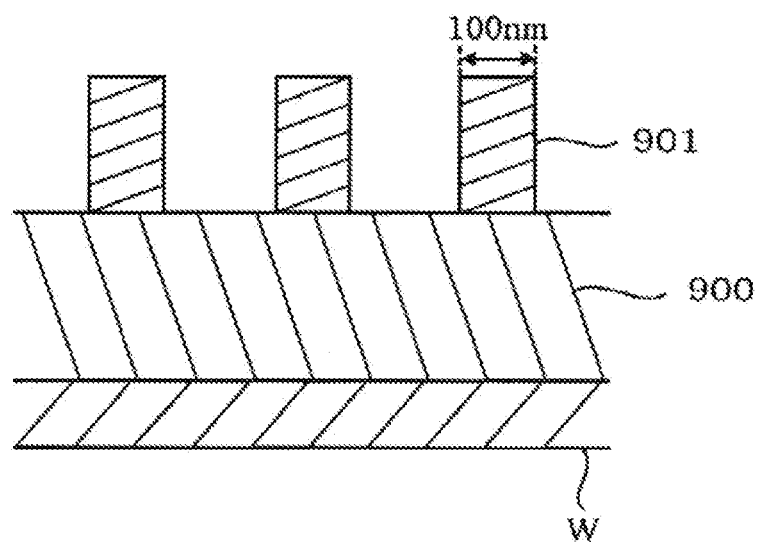
FIGS. 26A and 26B are vertical cross-sectional views showing the pattern structure in the surface of a wafer before and after an etching processing.

Next, processing performed in the processing system 6 will be described. FIG. 25 is a flowchart of the processing. First, a wafer W formed with a film to be etched 900 and a patterned resist film 901, for example, as shown in FIG. 26A being formed after completion of the developing treatment for the resist pattern is housed into the load port 50. Subsequently, the wafer W is carried by the carrier mechanism 60 to the alignment unit 70 and aligned there, and thereafter carried to the structure determination apparatus 80. When the wafer W is carried to the structure determination apparatus 80, for example, the line width and the dimension in the depth direction of the resist film 901 of the pattern structure in the surface of the wafer W are measured by the measurement unit 350 and the computation unit 351 (S701 in FIG. 25).

The measurement results measured in the structure determination apparatus 80 are outputted to the system control apparatus 40. The computation unit 354 of the system control apparatus 40 decides the etching condition so that the pattern structure in the surface of the wafer W after the etching processing has desired dimensions, based on the outputted measurement results and the correlation data stored in the memory unit 355 (S702 in FIG. 25). For example, when the measurement result of the line width of the resist film 901 is 100 nm, the etching processing time is decided to be 40 sec based on the correlation data between the etching time and the depth elimination amount in FIG. 24A in order to realize a target elimination amount in the depth direction of the film to be etched 900 of 200 nm. Further, in order to realize a target line width elimination amount of 40 nm (target line width elimination amount=measured line width (100 nm)–target line width (60 nm)), the supply flow rate of the etching gas is decided to be 38 cm$^3$/min based on the correlation data between the etching time and the flow rate of gas in FIG. 24B. When the etching processing time and the supply flow rate of the etching gas are decided, the setting of the etching processing condition in the system control apparatus 40 is changed (S703 in FIG. 25).

Figure 26B:
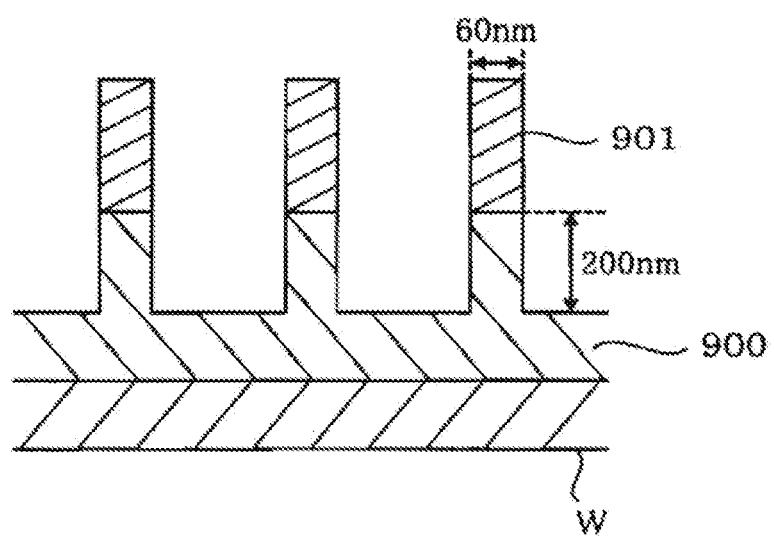

The wafer W whose dimensions of the pattern structure in the surface have been measured in the structure determination apparatus 80 is carried to the reduced-pressure processing apparatus 10, for example, by the carrier mechanism 60. The wafer W carried to the reduced-pressure processing apparatus 10 is subjected to the etching processing under the newly set etching processing condition (S704 in FIG. 25). This etching processing eliminates the film to be etched 900 and the resist film 901 into the desired dimensions as shown in FIG. 26B.

The wafer W for which the etching processing has been completed in reduced-pressure processing apparatus 10 is collected by the carrier mechanism 60 into the load port 50.

According to the sixth embodiment, it is possible to measure the dimensions of the pattern structure in the surface of the wafer W before the etching processing so as to set an optimal etching processing condition for target dimensions based on the measurement result of the dimensions and the previously obtained correlation data. Therefore, even if there is an error in dimension of the resist pattern at the stage before the etching processing, the error can be corrected at the time of the etching processing.

Further, since the measurement of the dimensions of the pattern structure in the wafer surface is carried out by Reflectometry, it is possible to rapidly measure the dimensions of the pattern structure in the surface wafer without breaking the wafer W.

Since the system control apparatus 40 can decide an optimal etching processing condition based on the measurement result of the pattern structure in the surface of the wafer W and the correlation data and change the setting of the etching processing condition, the etching processing condition can be automatically optimized. As a result of this, highly accurate processing for the wafer W can be performed with a high throughput.

In the sixth embodiment, the dimensions of the pattern structure in the surface of the wafer W are measured by Reflectometry, but the dimensions of the pattern structure in the wafer surface may be measured by another Scatterometry, for example, Ellipsometry. Besides, in this embodiment, the etching processing time and the supply flow rate of the etching gas are changed based on the measurement result of the pattern structure in the wafer surface, but it is also adoptable to change other etching processing conditions such as the pressure in the chamber 11, the power and the frequency of the first and second high-frequency power sources, the kind of gas, the temperature of the susceptor 12, the gap between the susceptor 12 and the upper electrode 13, and so on.

Besides, the above-described sixth embodiment relates to the etching processing after the formation of the resist pattern, but the present invention is also applicable to another etching processing which is performed, for example, in manufacturing process steps of a semiconductor device, such as an etching processing of a hard mask under the resist film, an etching processing at the time of removing the hard mask by peeling, and an etching processing at the time of removing polysilicon film.

It should be noted that the fifth and sixth embodiments illustrate examples of the present invention, and the present invention is not limited to those examples but can take various aspects. For example, the present invention is also applicable to processing systems which process a workpiece other than the wafer, for example, other substrates such as an FPD (Flat Panel Display) and a mask reticule for a photomask.

What is claimed is:

1. A method for processing a workpiece, comprising:
   measuring using Scatterometry a dimension of a surface structure of the workpiece in a depth direction and a dimension of the surface structure of the workpiece in a horizontal direction before an etching processing;
   setting a processing condition at the time of the etching processing based on the measured dimensions of the surface structure and correlation data so that the surface structure of the workpiece after the etching processing has at least one desired dimension; and
   thereafter, performing the etching processing for the workpiece under the set processing condition, wherein setting the processing condition at the time of the etching processsing includes:

calculating an elimination amount in a depth direction based on the measured dimension of the surface structure in the depth direction and desired dimension in the depth direction;

calculating an elimination amount in a horizontal direction based on the measured dimension of the surface structure in the horizontal direction and a desired dimension in the horizontal direction;

determining an etching processing time based on the elimination amount in the depth direction and the correlation data which correlates elimination amounts in the depth direction and etch processing times so that a dimension in a depth direction in the surface structure after the etching processing is the desired dimension in the depth direction; and determining a supply flow rate of an etching gas based on the elimination amount in the horizontal direction and the correlation data which correlates elimination amounts in the horizontal direction, etch processing times, and supply flow rates so that a dimension in a horizontal direction in the surface structure after the etching processing is the desired dimension in the horizontal direction; and wherein setting the processing condition further includes setting the processing condition based on the determination of the etching processing time and the supply flow rate.

2. The processing method as set forth in claim 1, wherein said processing condition setting step sets the processing condition so that dimensions at least in two dimensional directions of the surface structure after the etching processing are desired dimensions.

* * * * *